United States Patent
Miao et al.

(10) Patent No.: US 12,318,455 B2
(45) Date of Patent: *Jun. 3, 2025

(54) ANTI-HER2 ANTIBODY-DRUG CONJUGATE AND APPLICATION THEREOF

(71) Applicant: HANGZHOU ADCORIS BIOPHARMA CO., LTD., Hangzhou (CN)

(72) Inventors: Zhenwei Miao, Zhejiang (CN); Tong Zhu, Zhejiang (CN); B. Khasanov Alisher, Zhejiang (CN); Gang Chen, Zhejiang (CN); Zhaohui Li, Zhejiang (CN); Sheldon Cao, Zhejiang (CN)

(73) Assignee: HANGZHOU ADCORIS BIOPHARMA CO., LTD., Zhejiang (CN)

( * ) Notice: Subject to any disclaimer, the term of this patent is extended or adjusted under 35 U.S.C. 154(b) by 1075 days.

This patent is subject to a terminal disclaimer.

(21) Appl. No.: 16/075,475

(22) PCT Filed: Feb. 4, 2017

(86) PCT No.: PCT/CN2017/072888
§ 371 (c)(1),
(2) Date: Dec. 13, 2018

(87) PCT Pub. No.: WO2017/133682
PCT Pub. Date: Aug. 10, 2017

(65) Prior Publication Data
US 2019/0091345 A1 Mar. 28, 2019

(30) Foreign Application Priority Data
Feb. 4, 2016 (CN) .......................... 201610079677.8

(51) Int. Cl.
| | |
|---|---|
| *A61K 47/68* | (2017.01) |
| *A61K 31/427* | (2006.01) |
| *A61P 35/00* | (2006.01) |
| *C07D 401/12* | (2006.01) |
| *C07D 419/10* | (2006.01) |
| *C07D 419/12* | (2006.01) |
| *C07K 16/32* | (2006.01) |
| *A61K 38/07* | (2006.01) |
| *A61K 38/08* | (2019.01) |
| *A61K 39/00* | (2006.01) |
| *C07D 207/08* | (2006.01) |

(52) U.S. Cl.
CPC ........ *A61K 47/6849* (2017.08); *A61K 31/427* (2013.01); *A61K 47/6811* (2017.08); *A61K 47/6855* (2017.08); *A61P 35/00* (2018.01); *C07D 401/12* (2013.01); *C07D 419/10* (2013.01); *C07D 419/12* (2013.01); *C07K 16/32* (2013.01); *A61K 38/07* (2013.01); *A61K 38/08* (2013.01); *A61K 2039/505* (2013.01); *A61K 47/68031* (2023.08); *A61K 47/6857* (2017.08); *A61K 47/6863* (2017.08); *A61K 47/6869* (2017.08); *C07D 207/08* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally | .......... A61K 9/1272 264/4.1 |
| 9,814,784 B2 | 11/2017 | Park et al. | |
| 2019/0076438 A1 * | 3/2019 | Xue | .......... A61K 47/64 |

FOREIGN PATENT DOCUMENTS

| | | |
|---|---|---|
| WO | 2005/081711 A2 | 9/2005 |
| WO | 2013/173391 A1 | 11/2013 |
| WO | 2013/173392 A1 | 11/2013 |
| WO | 2014/107024 A1 | 7/2014 |
| WO | 2015/057876 A1 | 4/2015 |
| WO | WO-2015195904 A1 * | 12/2015 ........... C07K 16/32 |
| WO | 2016/123412 A1 | 8/2016 |

OTHER PUBLICATIONS

Guido et al (Curr Med Chem. 2008; 15(1):37-46) (Year: 2008).*
Clark et al (J. Med. Chem., 2014, 57 (12), pp. 5023-5038) (Year: 2014).*
Vajdos et al. (J Mol Biol. Jul. 5, 2002;320(2):415-28 (Year: 2002).*
Brown et al. (J Immunol. May 1996; 156(9):3285-91 (Year: 1996).*
Goodman (American Health & Drug Benefits Apr. 2013; 6(3): 72-76) (Year: 2013).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042) (Year: 1997).*
Furthermore, Jain RK (Scientific American, Jul. 1994,58-65) (Year: 1994).*
Hogenesch et al (J Control Release. Dec. 10, 2012; 164(2): 183-186.) (Year: 2012).*
Hait (Nature Reviews/Drug Discovery, 2010, 9, pp. 253-254) (Year: 2010).*

(Continued)

*Primary Examiner* — Brian Gangle
*Assistant Examiner* — Andrea K McCollum
(74) *Attorney, Agent, or Firm* — NKL Law; Allen Xue

(57) ABSTRACT

An anti-human epidermal growth factor receptor 2 (anti-HER2) antibody-drug conjugate or a pharmaceutically acceptable salt thereof, and an application of the anti-HER2 antibody-drug conjugate for preparing an antitumor 5 pharmaceutical product.

14 Claims, 4 Drawing Sheets
Specification includes a Sequence Listing.

(56) References Cited

OTHER PUBLICATIONS

Gravanis et al. (Chin Clin Oncol, 2014, 3, pp. 1-5) (Year: 2014).*
Beans (PNAS 2018; 115(50): 12539-12543) (Year: 2018).*
Howie et al (Clin Cancer Res (2019) 25 (10): 2949-2955) (Year: 2019).*
Panowski et al., "Site-specific antibody drug conjugates for cancer therapy," mAbs, vol. 6, No. 1, pp. 34-45 (2014).
Beck et al., "Antibody-drug conjugates," mAbs, vol. 6 no. 1, pp. 15-17 (2014).
International Search Report mailed in International Patent Application No. PCT/CN2017/072888 (May 5, 2017).

* cited by examiner

ANTI-HER2 ANTIBODY-DRUG CONJUGATE AND APPLICATION THEREOF

CROSS-REFERENCE TO RELATED APPLICATION(S)

This application is a U.S. national stage filing under 35 U.S.C. § 371 of International Patent Application No. PCT/CN2017/072888, filed on Feb. 4, 2017, which application claims the benefit of Chinese Patent Application No. 201610079677.8, filed on Feb. 4, 2016, the entire contents of each of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 64,240 bytes ASCII (Text) file named "P2018-1431-1PCUS-208330-9007-US01-SEQ-LIST-10-06-23.txt," created on Oct. 5, 2023.

FIELD OF INVENTION

The present invention relates to the field of bio-medicine and, in particular, to an anti-HER2 antibody-drug conjugate.

BACKGROUND OF INVENTION

HER family of receptor tyrosine kinase is an important mediator for cell growth, differentiation and survival. This family of receptors includes four distinct members: HER1 (EGFR or ErbB1), HER2 (ErbB2 or p185neu), HER3 (ErbB3) and HER4 (ErbB4 or tyro2).

In addition to HER2 itself, binding of specific ligands to the outer functional domains of EGFR, HER3 and HER4 results in the formation of homodimeric or heterodimeric complexes with kinase activity, in which HER2 is the preferred part. Although HER2 does not directly interact with HER-activating ligands, it is well certain that its kinase is capable of making a heterodimer comprising HER2 transmit signal and increasing the binding affinity of ligands to EGFR or HER3. The formation of HER2 dimer triggers a series of processes in cells that ultimately leads to increase in cell movement, cell survival and proliferation, and anti-apoptotic activity.

In the development of cancer-targeted therapies, a successful strategy is to use monoclonal antibodies (mAb) to localize antigenic determinants on the surface of tumor cells, thereby targeting and killing cancer cells. According to this principle, antibodies can be used to target HER2 antigen on the surface of tumor cells to kill cancer cells. Trastuzumab (Herceptin) is a humanized anti-HER2 monoclonal antibody that binds to region IV of the surface region of HER2 cells and is used in combination with chemotherapeutic drugs to treat HER2-positive breast cancer. However, clinically treatments comprising trastuzumab are very limited, especially when HER2-positive cancer cells fail to respond or respond poorly to trastuzumab. This prompts people to start looking for new treatments for HER2-positive malignancies.

A new specific treatment for cancer cell antigens is the use of antibodies as carriers to carry toxic small molecules into cancer cells and then use the dissociated small molecules to kill cancer cells. T-DM1 (Trastuzumab-MCC-DM1) is the first antibody-drug conjugates (ADC) for solid tumors and is also a new treatment for HER2-positive metastatic breast cancer. In T-DM1, maytansinoid (DM1) with anti-tubulin formation is coupled to trastuzumab through a small linker MCC. T-DM1 is able to inhibit HER2-positive tumors that are sensitive and insensitive to trastuzumab, and shows better safety in preclinical toxicological experiment.

In addition to trastuzumab, pertuzumab (Perjeta) is also a humanized HER2-specific monoclonal antibody. Unlike trastuzumab, pertuzumab binds to region II of the surface region of HER2 cells, thereby preventing HER2 from binding to other members of HER family. Pertuzumab as a drug alone and in combination with chemotherapy, trastuzumab and T-DM1 have clinically demonstrated anticancer effects against ovarian cancer, non-small cell lung cancer, prostate cancer, breast cancer and gastric cancer.

Attachment of a drug moiety to an antibody with conventional antibody disulfide bond reduction or lysine side chain amine group generally results in heterogeneous antibody drug mixture, because the drug moiety can be attached to a number of sites on the antibody. For example, in the above T-DM1, an antibody is usually linked to varying amounts, 0-8 of drug moieties. Moreover, even for conjugates with the same coupling number, each subcomponent may be a heterogeneous mixture in which the drug moiety is attached to various sites on the antibody. Analytical and preparative methods may be difficult to isolate and characterize the heterogeneous antibody drug conjugates mixture produced by the coupling reaction.

Those skilled in the art are committed to developing new, more effective antibody drug conjugates.

SUMMARY OF INVENTION

The purpose of the invention is to provide an anti-HER2 antibody-drug conjugate and application thereof.

In the first aspect of the invention, an antibody-drug conjugate or a pharmaceutically acceptable salt thereof is provided, the structure of the antibody-drug conjugate is as shown in formula I:

$$Ab\text{-}(L\text{-}D)n \qquad \qquad \text{I}$$

wherein:
Ab is an antibody;
L is absent or a linker connecting the antibody and the drug;
D is a small molecule drug that inhibits tumor cells;
n is the number of drug coupled to the antibody;
"-" is a bond or a linker.

In another preferred embodiment, the light chain constant region of the antibody-drug conjugate is coupled with at least one drug molecule (preferably one drug molecule per light chain constant region), and the drug molecule is linked to a lysine site of the light chain constant region.

In another preferred embodiment, the light chain constant region of the antibody comprises EKH motif and the drug molecule is linked to a lysine (K) site of the motif.

In another preferred embodiment, the light chain constant region of the antibody comprises YEKHK (SEQ ID NO: 59) motif and the drug molecule is linked to the first lysine (K) site of the motif.

In another preferred embodiment, the light chain constant region of the antibody comprises ADYEKHK (SEQ ID NO: 60) motif and the drug molecule is linked to the first lysine (K) site of the motif.

In another preferred embodiment, the drug molecule is a small molecule drug that inhibits tumor cells.

In another preferred embodiment, n is the average number of coupled drugs in the antibody-drug conjugate, preferably n is from 1 to 4, preferably from 1.5 to 3.5, more preferably from 1.8 to 2.

In another preferred embodiment, the antibody is selected from: monoclonal antibodies, antibody fragments (including Fab, Fab', F (ab')$_2$ and Fv fragments), diabodies, single domain antibodies, chimeric antibodies, humanized antibodies and single chain antibodies.

In another preferred embodiment, the antibody is an anti-HER2 antibody.

In another preferred embodiment, the antibody is pertuzumab and a biosimilar thereof.

In another preferred embodiment, the sequence of the heavy chain variable region of the antibody is selected from SEQ ID NOs:30-57.

In another preferred embodiment, the sequence of the heavy chain constant region of the antibody is as shown in SEQ ID NO:58.

In another preferred embodiment, the sequence of the light chain variable region of the antibody is selected from SEQ ID NOs:1-28.

In another preferred embodiment, the sequence of the light chain constant region of the antibody is as shown in SEQ ID NO:29.

In another preferred embodiment, the drug is dolastatin or a derivative thereof.

In another preferred embodiment, the light chain constant region comprises an amino acid sequence as shown in SEQ ID NO: 29, and the drug molecule is linked to the site of the lysine at position 81 of the amino acid sequence as shown in SEQ ID NO: 29.

In another preferred embodiment, the structure of D is as shown in formula III:

wherein, Y is O or NH,
the wavy line indicates the connection position with L,
X is $CH_2N_3$ or

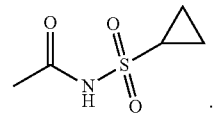

In another preferred embodiment, the structure of the antibody-drug conjugate is as shown in formula III:

$$Ab\text{-}(L^1\text{-}L^2\text{-}D)_n,\qquad\text{III}$$

in formula III, the structure of $L^1$-$L^2$ is selected from L-1, L-2 or L-3:

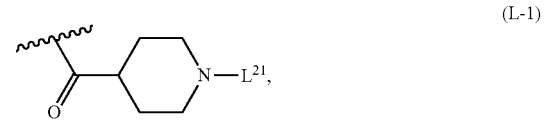

(L-1)

(L-2)

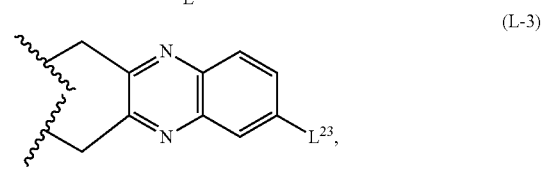

(L-3)

wherein $L^{21}$, $L^{22}$, $L^{23}$ are linkers independently selected from —(CH2)n-, —(CH2CH2O)n-, Val-Cit, Ala-Ala-Asn, or a combination thereof;

Ab, D, n are defined as above;

the wavy line indicates the connection position with antibody.

In another preferred embodiment, the antibody-drug conjugate is selected from: ZV0201, ZV0202, ZV0203, ZV0204, ZV0205, ZV0230, ZV0207, ZV0231, ZV0232,

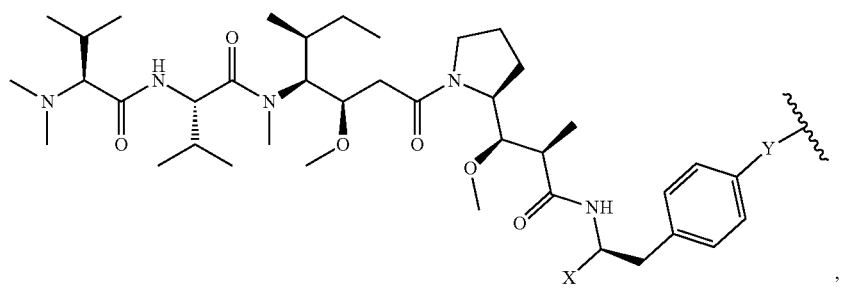

II wherein the structure of conjugate ZV0203 is shown as follows:
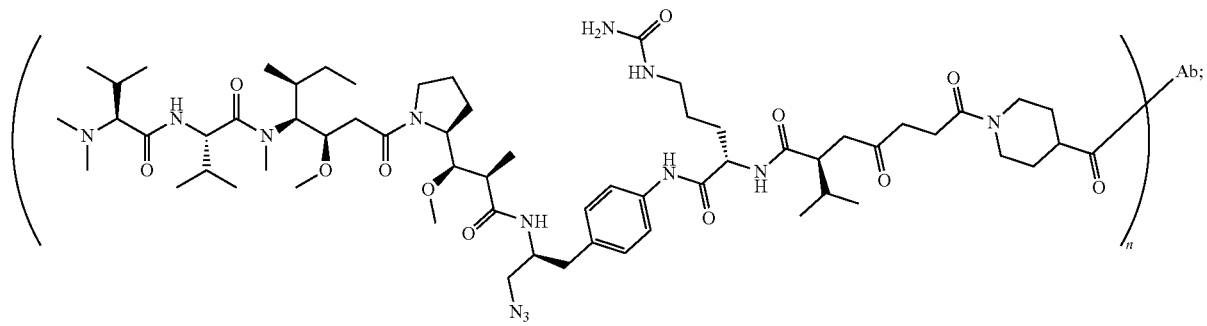
the structure of conjugate ZV0230 is shown as follows:
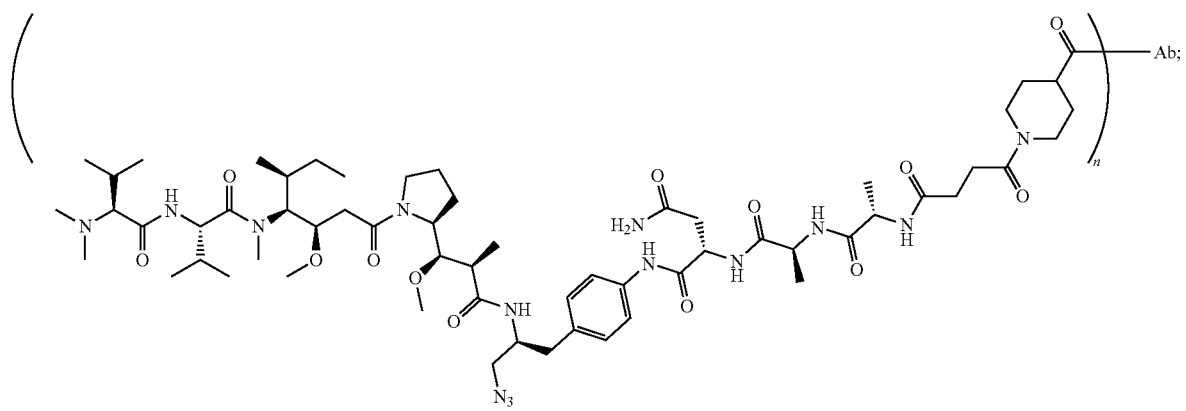
the structure of conjugate ZV0201 is shown as follows:
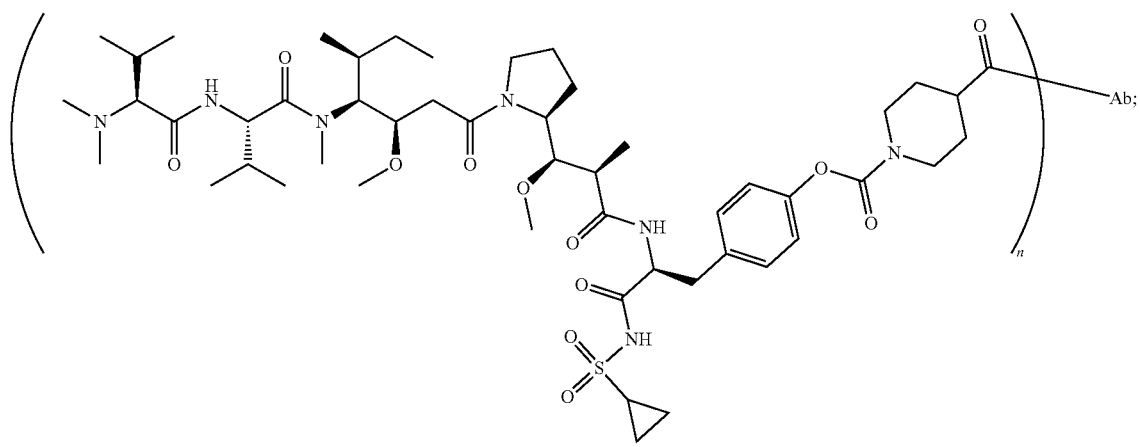

the structure of conjugate ZV0207 is shown as follows:
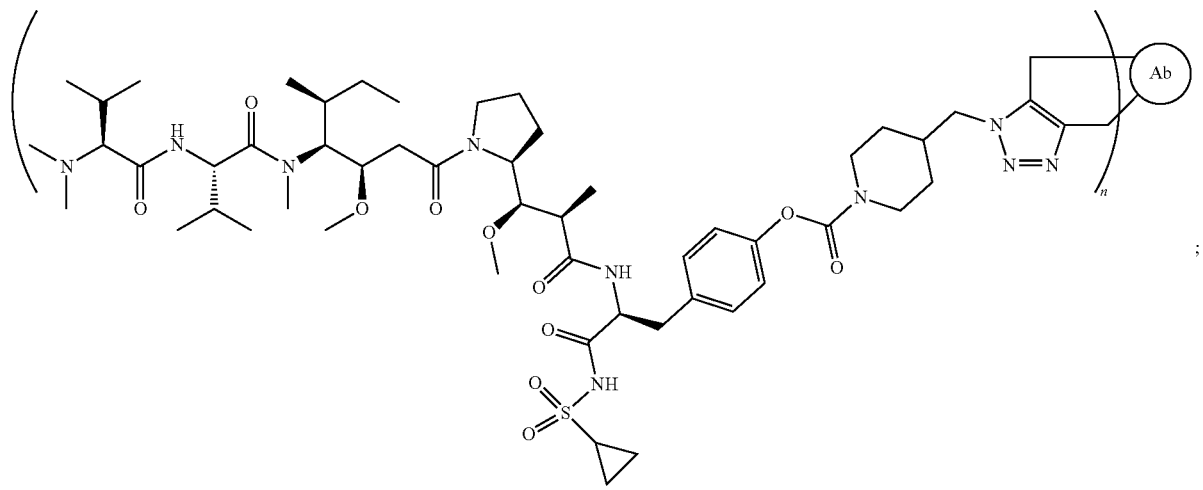
the structure of conjugate ZV023.1 s shown as follows:
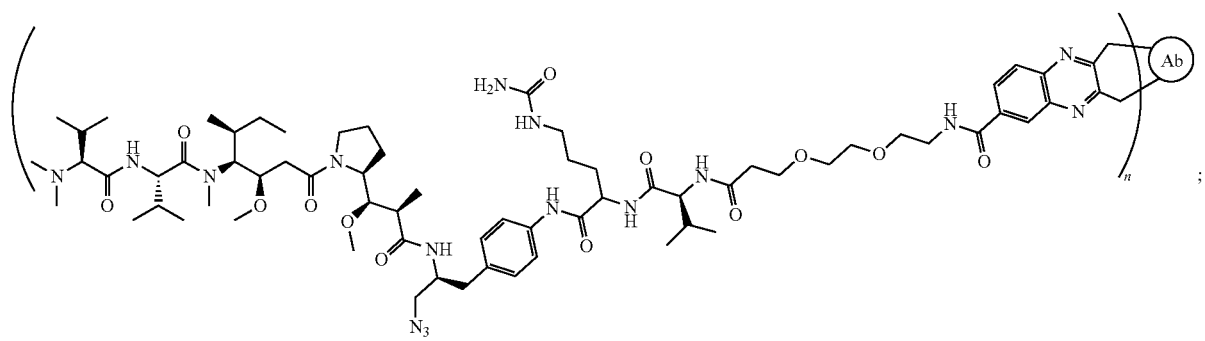
the structure of conjugate ZV0232 is shown as follows:
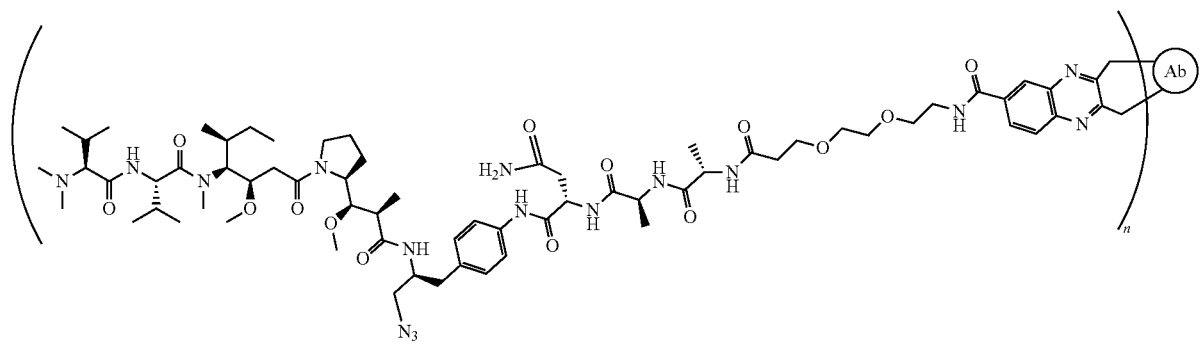

the structure of conjugate ZV0202 is shown as follows:

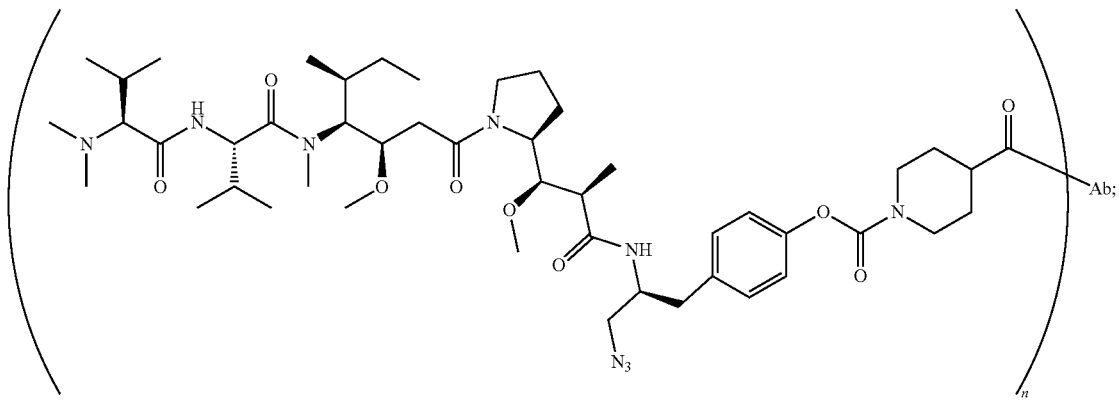

the structure of conjugate ZV0204 is shown as follows:

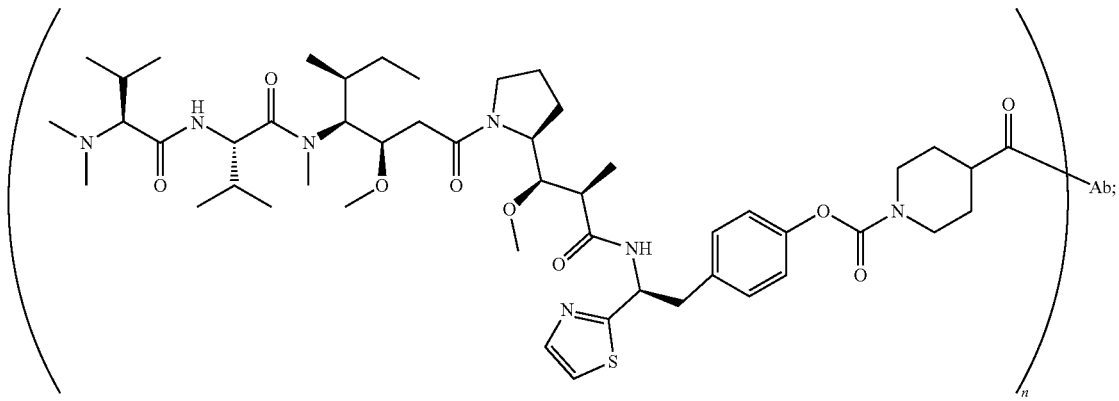

the structure of conjugate ZV0205 is shown as follows:

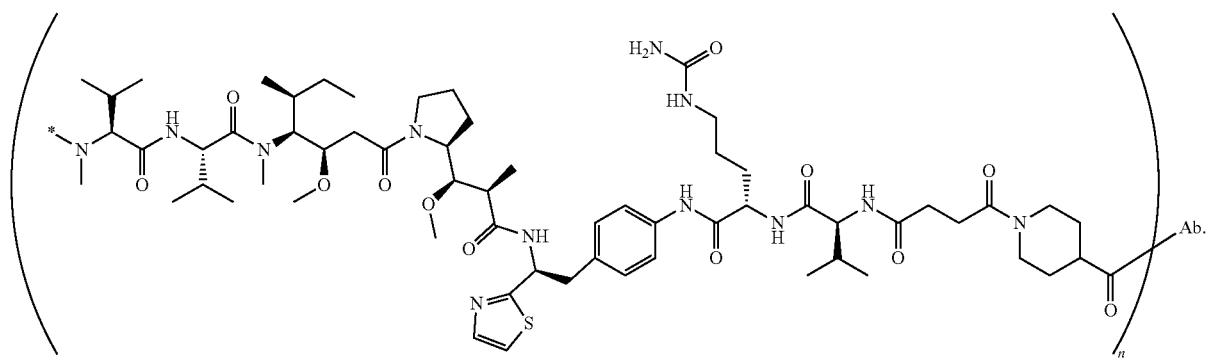

In the second aspect of the invention, a pharmaceutical composition is provided, which comprises: the antibody-drug conjugate according to the first aspect of the present invention, and a pharmaceutically acceptable carrier.

In the third aspect of the invention, a use of the antibody-drug conjugate according to the first aspect of the present invention is provided for preparing anti-tumor drugs.

In another preferred embodiment, the tumor includes cancers such as breast cancer, gastric cancer, ovarian cancer, and lung cancer.

In the fourth aspect of the invention, a method for treating or preventing a tumor is provided, which comprises the step of administering to a subject in need thereof the antibody-drug conjugate according to the first aspect of the present invention; or the pharmaceutical composition according to the second aspect of the present invention.

In the fifth aspect of the invention, a preparation method for the antibody-drug conjugate according to the first aspect of the present invention is provided, which comprises the following steps:
configuring a reaction system including an antibody and a free drug molecule, and then performing a coupling reaction to prepare the antibody-drug conjugate, wherein the drug molecule includes a linker.

In another preferred embodiment, the pH of the reaction system is from 6.5 to 8.0; preferably the pH is from 6.8 to 7.8; more preferably the pH is from 7.0 to 7.5, such as 7.1, 7.2, 7.3, and 7.4.

In another preferred embodiment, the drug molecule is linked to a lysine (K) site of the light chain constant region of the antibody.

In another preferred embodiment, the reaction time is from 3 h to 16 h.

In another preferred embodiment, the molar ratio of the antibody to the drug molecule is from 1-2: 3-20; preferably from 1: 6-10.

It should be understood that, within the scope of the present invention, the technical features specifically described above and below (such as in the Examples) can be combined with each other, thereby constituting a new or preferred technical solution which needs not be described one by one.

DESCRIPTION OF THE DRAWINGS

FIG. 1 shows the analysis results of the antibody drug conjugate of the present invention.

DETAILED DESCRIPTION OF THE INVENTION

Figure 1A:
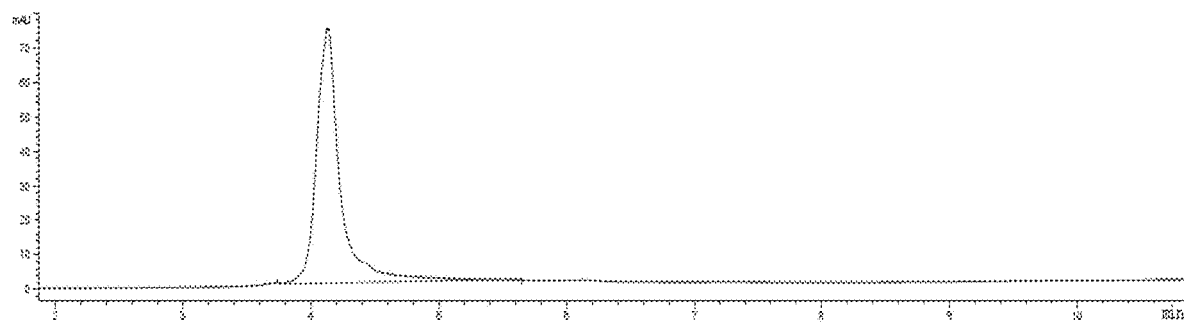
FIG. 1A shows the results of HIC analysis of unconjugated antibodies.
Figure 1B:
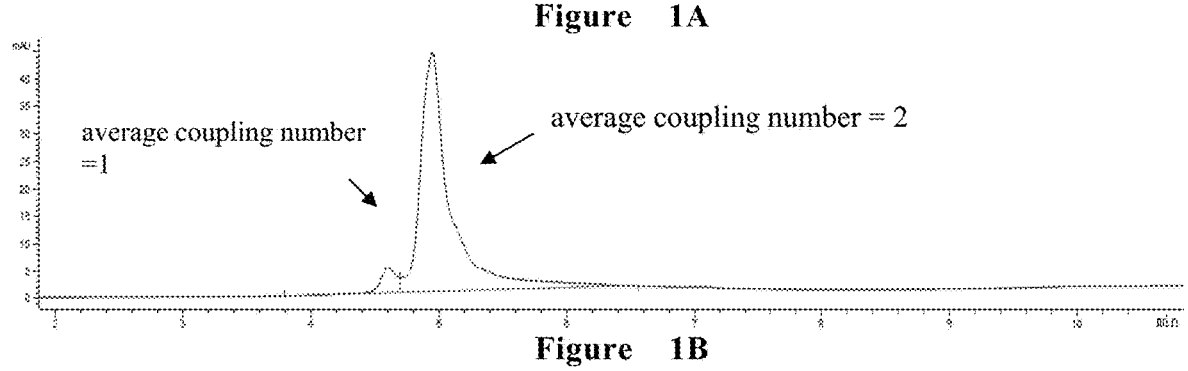
FIG. 1B shows the results of HIC analysis of ZV0201.
Figure 1C:
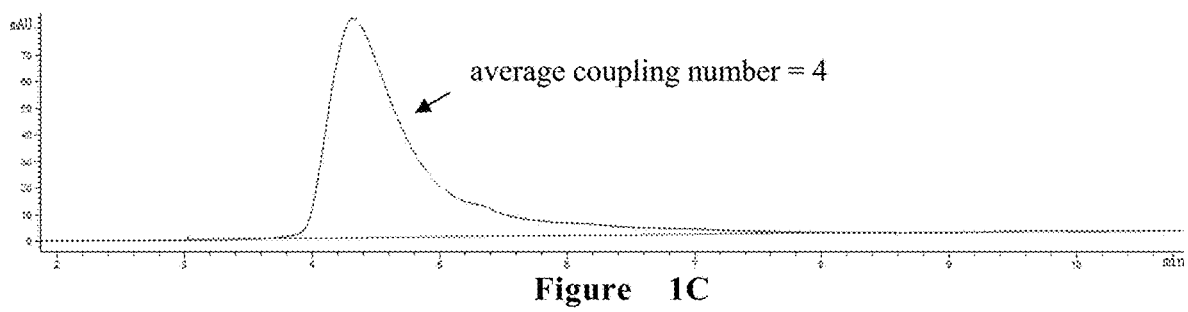
FIG. 1C shows the results of HIC analysis of ZV0223.

Through extensive and intensive researches, the inventors have obtained an anti-HER2 antibody-drug conjugate. The experimental results show that said antibody-drug conjugate has a significant anti-tumor effect. The invention also provides pharmaceutical use of the anti-HER2 antibody-drug conjugate and its role in inhibiting or preventing tumors.

The present invention generally relates to antibody-drug conjugates, and more particularly, the present invention relates to antibody drug conjugates having therapeutic applications. The anti-HER2 antibody can be conjugated to a chemotherapeutic drug or toxin by a linker. The invention also relates to methods of treating mammalian cells or related pathological conditions using an anti-HER2 antibody-drug conjugate.

The present invention uses a linker (L) moiety which is capable of coupling to a specific lysine position of the constant region of the antibody, or to a disulfide-reduced cysteine. After one-step hydrophobic purification (HIC), antibody-conjugated drugs with site-directed and quantitative coupling are obtained.

The antibody (Ab) is coupled to the drug moiety (D) via a linker (L, including L1 or L2) through a disulfide-reduced cysteine or a reactive lysine of the constant region to form an antibody-drug conjugate: Ab-(L-D)n, wherein n is 1-4. Coupling methods and therapeutic use of the antibody drug conjugates are disclosed in the present invention.

Before describing the present invention, it should be understood that the invention is not limited to the described particular methodology and experimental conditions, as such methods and conditions may be varied. It is also to be understood that the terminology used herein is only for the purpose of describing particular embodiments, and is not intended to be limiting, and the scope of the invention will be limited only by the appended claims.

Unless otherwise defined, all technical and scientific terms used herein have the same meaning as commonly understood by the ordinary skilled in the art to which this invention belongs. As used herein, the term "about" when used in reference to a particular listed value means that the value can vary from the listed value by no more than 1%. For example, as used herein, the expression of "about 100" includes all values between 99 and 101 (for example, 99.1, 99.2, 99.3, 99.4, etc.).

Although any methods and materials similar or equivalent to those described in this disclosure may be used in the practice or testing of the present invention, the preferred methods and materials are exemplified herein.

The present invention provides two types of coupling methods. Small molecules of toxin are coupled to an antibody through a specific linker, and the lethality of the antibody against tumor cells are greatly improved without changing the affinity of the antibody.

The term "antibody" or "immunoglobulin" as used herein refers to a heterotetrameric glycoprotein with the same structural feature of about 150,000 daltons, which consists of two identical light chains (L) and two identical heavy chains (H). Each light chain is linked to a heavy chain by a covalent disulfide bond, and the numbers of disulfide bonds between the heavy chains of different immunoglobulin isoforms are different. Each heavy and light chain also has regularly spaced intrachain disulfide bonds. Each heavy chain has a variable region (VH) at one end, followed by a plurality of constant regions. Each light chain has a variable region (VL) at one end and a constant region at the other end; the constant region of the light chain corresponds to the first constant region of the heavy chain; and the variable region of the light chain corresponds to the variable region of the heavy chain. There is an interface formed between the variable regions of the light and heavy chains by particular amino acid residues.

As used herein, the term "variable" means that some certain portions of the variable region of an antibody differ in sequence and contribute to the binding and specificity of each particular antibody to its particular antigen. However, the variability is not evenly distributed throughout the antibody variable region. It is concentrated in three regions in the light and heavy chain variable regions called complementary determining regions (CDRs) or hypervariable regions. The relatively conserved portions of the variable regions are referred as framework regions (FRs). The variable regions of the natural heavy and light chains each comprises four FR regions, which are in a substantially β-folded configuration, and are linked by three CDRs that form the linker ring and, in some cases, form a partial β-folded structure. The CDRs in each chain stand close together through FR regions and form the antigen-binding site of the antibody together with the CDRs of the other chain (see Kabat et al., NIH Publ. No. 91-3242, Vol. I, 647-669 (1991)). Constant regions are not directly involved in the binding of the antibodies to the antigens, but they exhibit different effector functions, such as antibody-dependent cytotoxicity involved in antibodies.

The 'light chain' of vertebrate antibody (immunoglobulin) could be divided into two distinct types (κ or λ) according to the amino acid sequences of constant region. Based on the amino acid sequences of heavy chain constant region, immune globulins could be divided into different species. There are five classes of immunoglobulins: IgA, IgD, IgE, IgG and IgM, some of them could be further divided into subclass: IgG1, IgG2, IgG3, IgG4, IgA and IgA2. The heavy chain constant regions corresponding to different classes of immunoglobulins could be named as α, δ, ε, γ and μ. The subunit structures and 3D configurations of different immunoglobulins are well known to those skilled in the art.

In general, the antigen-binding properties of an antibody can be described by three specific regions located in the heavy chain and light chain variable region, referring as variable regions (CDRs), and this segment is separated into four framework regions (FRs). The sequences of four FRs amino acids are relatively conservative and do not directly participate in the binding reaction. A cyclic structure are formed by these CDRs, β-folds formed by the FRs between them are close to each other in the spatial structure, and the CDRs on the heavy chains and the CDRs on the corresponding light chains constitute the antigen-binding sites of the antibody. The amino acid sequence of the same type of antibody can be compared to determine which amino acids have constituted the FR or CDR region.

The present invention includes not only intact antibodies but also fragments of antibodies or fusion proteins formed by antibodies with other sequences with immunological activity. Accordingly, the present invention also includes fragments, derivatives and analogs of said antibodies.

As used herein, the terms "fragments", "derivatives" and "analogs" refer to the polypeptides that substantially maintain the same biological function or activity of the antibodies of the present invention. The polypeptide fragments, derivatives or analogs of the present invention may be (i) a polypeptide with one or more conservative or non-conservative amino acid residues (preferably the conservative amino acid residues) being substituted, while such a substituted amino acid residue may or may not be encoded by a genetic code, or (ii) a polypeptide having substituted group (s) in one or more amino acid residues, or (iii) a polypeptide formed by fusion of the mature polypeptide with another compound (such as the compound that prolongs the half life of the polypeptide, such as polyethylene glycol), or (iv) a polypeptide with additional amino acid sequence fused to said polypeptide sequence (such as fusion proteins formed by fusion with leader sequence, secretion sequence or sequence used to purify the polypeptide or proprotein sequence, or a fusion protein formed with a 6His tag. According to the teachings of the present application, these fragments, derivatives and analogs are within the scope commonly known by the skilled person.

In the present invention, the antibody of the present invention also includes the conserved variants thereof which refers to the polypeptides formed by substituting at most 10, preferably at most 8, more preferably at most 5, and most preferably 3 amino acid of the amino acid sequence of the polypeptide of the present invention with the amino acid having similar or analogous properties. These conservative variant polypeptides are preferably formed by carrying out the amino acid substitution according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The sequence of the DNA molecule of the antibody or fragment thereof of the present invention can be obtained by conventional techniques such as PCR amplification or genomic library screening. In addition, the coding sequences of the light and heavy chains can be fused together to form a single chain antibody.

Once the relevant sequence is obtained, the relevant sequence can be obtained in bulk using the recombination method. It is usually cloned into a vector, transferred to a cell, and then isolated from the host cell after proliferation by conventional methods.

In addition, artificial synthetic methods can be used to synthesize relevant sequences, especially when the length of the fragment is short. In general, a very long fragment can be obtained by first synthesizing multiple small fragments and then ligating them.

At present, DNA sequences encoding the antibody of the present invention (or fragments thereof, or derivatives thereof) can be completely obtained by chemical synthesis. Then the DNA sequence can be introduced into a variety of current DNA molecules (or vectors) and cells known in the art. In addition, mutations can also be introduced into the protein sequences of the present invention by chemical synthesis.

The present invention also relates to vectors comprising the suitable DNA sequence as described above and a suitable promoter or control sequence. These vectors can be used to transform suitable host cells to enable them to express proteins.

Host cells can be prokaryotic cells, such as bacterial cells; or lower eukaryotic cells, such as yeast cells; or higher eukaryotic cells, such as mammalian cells.

For example, the antibody of the present invention can be produced by the following method.

First, an expression vector comprising a nucleotide sequence encoding the antibody of the present invention and an expression regulatory sequence operably linked to the sequence is provided.

The term "expression regulatory sequence" as used herein generally refers to a sequence involved in the control of expression of a nucleotide sequence. Expression regulatory sequences include promoter and termination signals operably linked to a nucleotide sequence of interest. They usually also include the sequences required for proper translation of the nucleotide sequence. "Operably linked" means that portions of a linear DNA sequence are capable of affecting the activity of other portions of the same linear DNA sequence. For example, if a promoter or enhancer increases the transcription of a coding sequence, it is operably linked to the coding sequence.

DNA sequences encoding the monoclonal antibody of the present invention can be produced by conventional means well known to those skilled in the art. For example, a nucleotide sequence encoding the heavy chain variable region and the light chain variable region of the monoclonal antibody can be artificially synthesized or amplified by PCR according to the sequences disclosed in the present invention. These nucleotide sequences are then inserted into appropriate expression vectors by selection of appropriate cleavage sites using various methods well known in the art, and they are placed in front of the coding sequence of the heavy chain constant region and the coding sequence of the light chain constant region carried by expression vector (s), respectively and in the same reading frame. The expression vectors used in the present invention are various commercially available expression vectors known to those skilled in the art, such as pPIC9K.

Subsequently, an appropriate host cell is transformed with the expression vector obtained above. "Host cells" generally include prokaryotic cells and eukaryotic cells. Examples of commonly used prokaryotic host cells include *Escherichia coli, Bacillus subtilis* and the like. Commonly used eukaryotic host cells include yeast cells, insect cells, and mammalian cells. In the present invention, mammalian cells are preferred. Mammalian cell lines are usually used as host cells for expression of eukaryotic cell-derived polypeptides. Propagation of mammalian cells in culture is well known in the art. See "tissue culture", Academic Press, Kruse and Patterson ed. (1973), this article is incorporated herein by reference. Preferred mammalian cells are a number of commercially available immortalized cell lines. These immortalized cell lines include, but are not limited to, Chinese hamster ovary (CHO) cells, Vero cells, HeLa cells, baby hamster kidney (BHK) cells, monkey kidney cells (COS), human hepatocyte cancer cells (such as Hep G2), and many other cell lines. They provide post-translational modifications to protein molecules, including correct folding, proper disulfide bond formation, and glycosylation at the correct site. Although in the following examples, the present invention exemplifies only examples in which CHO cells are used as host cells, those skilled in the art will recognize that the present invention can also employ the above cell lines by reading the detailed description and specific examples of the present invention.

There are many methods for transformation of host cells with expression vectors, and the transformation procedure used depends on the host to be transformed. Methods for introducing heterologous polynucleotides into mammalian cells are known in the art, which include dextran mediated transfection, calcium phosphate precipitation, Polybrene (1,5-dimethyl-1,5-diazaundecamethylene polymethobromide) mediated transfection, protoplast fusion, electroporation, liposome-mediated transfection, and direct microinjection of DNA into the nucleus. In the present invention, preferred methods are electroporation or liposome-mediated methods and the like. For example, a liposome assay kit from Invitrogen can be used to transfect host cells such as CHO cells.

The transformed host cells are then cultured under conditions suitable for expression of the antibody of the present invention. Then the antibody of the present invention are purified and obtained using conventional immunoglobulin purification steps such as protein A-Sepharose, hydroxyapatite chromatography, gel electrophoresis, dialysis, ion exchange chromatography, hydrophobic chromatography, molecular sieve chromatography or affinity chromatography, etc, which are conventional separation and purification means well known to those skilled in the art.

The obtained monoclonal antibodies can be identified by conventional means. For example, the binding specificity of a monoclonal antibody can be determined by immunoprecipitation or an in vitro binding assay such as radioimmunoassay (RIA) or enzyme-linked immunosorbent assay (ELISA). The binding affinity of a monoclonal antibody can be determined, for example, by Scatchard analysis of Munson et al, Anal. Biochem., 107: 220 (1980).

The antibody of the present invention can be expressed intracellularly, or on the cell membrane, or secreted out of the cell. If desired, recombinant proteins can be isolated and purified by various separation methods using their physical, chemical and other properties. These methods are well known to those skilled in the art. Examples of such methods include, but are not limited to, conventional renaturation treatments, treatment with a protein precipitant (salting-out method), centrifugation, penetration-breaking bacteria, sonication, ultracentrifugation, molecular sieve chromatography (gel filtration), adsorption chromatography, ion-exchange chromatography, high performance liquid chromatography (HPLC) and various other liquid chromatography techniques and combinations of these methods.

In a preferred embodiment of the invention, the antibody in the antibody-drug conjugate according to the invention is an anti-HER2 antibody.

In a preferred embodiment of the invention, the amino acid sequence of the light chain variable region of the anti-HER2 antibody is selected from the group consisting of:

```
                                           (SEQ ID NO: 1)
DIQMTQSPSSLSASVGDRVTITCKASQDVSIGVAWYQQKPGKAPKLLIYS

ASYRYTGVPSRFSGSGSGTDFTLTISSLQPEDFATYYCQQYYIYPYTFGQ

GTKVEIK;

(SEQ ID NO: 2)
DIQMTQSPSSLSASVGDRVTITCKASQDVSIGVAWYQQKPGKAPKLLLYS

ASYRYTGVPSRFSGSGSGTDYTLTISSLQPEDFATYYCQQYYIYPYTFGG

GTKLEIKRT;

(SEQ ID NO: 3)
EIVLTQSPGTLSLSPGERATLSCKASQDVSIGVAWYQQKPGQAPRLLIYS

ASYRYTGIPDRFSGSGSGTDFTLTISRLEPEDFAVYYCQQYYIYPYTFGG

GTKLEIKRT;
```

(SEQ ID NO: 4)
EIVMTQSPATLSVSPGERATLSCKASQDVSIGVAWYWKPGQAPRLLIYSA
SYRYTGIPARFSGSGSGTEFTLTISSLQSEDFAVYYCQQYYIYPYTFGGG
TKLEIKRT;

(SEQ ID NO: 5)
EIVMTQPPTLSLSPGERVTLSCKASQDVSIGVAWYQQKPGQAPRLLIYSA
SYRYTSIPARFSGSGSGTDFTLTISSLQPEDFAVYYCQQYYIYPYTFGGG
TKLEIKRT;

(SEQ ID NO: 6)
AIRMTQSPSSFSASTGDRVTITCKASQDVSIGVAWYQQKPGKAPKLLIYS
ASYRYTGVPSRFSGSGSGTDFTLTISCLQSEDFATYYCQQYYIYPYTFGG
GTKLEIKRT;

(SEQ ID NO: 7)
DIQMTQSPSSLSASVGDRVTITCKASQDVSIGVAWYQQKPGKAPKLLIYS
ASYRYTGVPSRFSGSGSGTDFTFTISSLQPEDIATYYCQQYYIYPYTFGG
GTKLEIKRT;

(SEQ ID NO: 8)
DIQMTQSPSSLSASVGDRVTITCKASQDVSIGVAWYQQKPGKVPKLLIYS
ASYRYTGVPSRFSGSGSGTDFTLTISSLQPEDVATYYCQQYYIYPYTFGG
GTKLEIKRT;

(SEQ ID NO: 9)
AIQLTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGG
GTKLEIKRT;

(SEQ ID NO: 10)
DIQMTQSPSTLSASVGDRVTITCKASQDVSIGVAWYQQKPGKAPKLLIYS
ASYRYTGVPSRFSGSGSGTEFTLTISSLQPDDFATYYCQQYYIYPYTFGG
GTKLEIKRT;

(SEQ ID NO: 11)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 12)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 13)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 14)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 15)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 16)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 17)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 18)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 19)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 20)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 21)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 22)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYFGQG
TKVEIK;

(SEQ ID NO: 23)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 24)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 25)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 26)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 27)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK;

(SEQ ID NO: 28)
DIQMTQSPSSLSASVGDRVTITCKASQDVSIGVAWYQQKPGKAPKLLIYS
ASYRYTGVPSRFSGSGSGTDFTLTISSLQPEDFATYYCQQYYIYPYTFGQ
GTKVEIK.

In a preferred embodiment of the invention, the amino acid sequence of the light chain constant region of the anti-HER2 antibody is:

(SEQ ID NO: 29)
RTVAAPSVFIFPPSDEQLKSGTASVVCLLNNFYPREAKVQWKVDNALQGN
SQESVTEQDSKDSTYSLSSILTLSKADYE<u>K</u>HKVYACEVTHQGLSSPVTKS
FNRGEC.

Wherein, the underlined K is a lysine residue which is preferably linked to a drug molecule in the present invention.

In a preferred embodiment of the invention, the amino acid sequence of the heavy chain variable region of the anti-HER2 antibody is selected from the group consisting of:

(SEQ ID NO: 30)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYINGQGTLVTVSS;

(SEQ ID NO: 31)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 32)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 33)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 34)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 35)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 36)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 37)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 38)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 39)
EVQLVESGGGLVQPGGSLRLSCAASGFTFTDYTMDWVRQAPGKGLEWVAD
VNPNSGGSIYNQRFKGRFTLSVDRSKNTLYLQMNSLRAEDTAVYYCARNL
GPSFYFDYWGQGTLVTVSS;

(SEQ ID NO: 40)
EVQLVESGGGLVQPGGSLRLSCAASGFTFTDYTMDWVRQAPGKGLEWVSD
VNPNSGGSIYNQRFKGRFTISRDNSKNTLYLQMNSLRAEDTAVYYCAKNL
GPSFYFDYWGQGTTLTVSS;

(SEQ ID NO: 41)
EVQLVESGGGLVQPGGSLRLSCAASGFTFTDYTMSPRQAPGKGLEWVSDV
NPNSGGSYYADSVKGRFTISRDNSKNTLYLQMNSLRAEDTAVYYCAKNLG
PSFYFDYWGQGTTLTVSS;

(SEQ ID NO: 42)
QVQLVQSGSELKKPGASVKVSCKASGFTFTDYTMDWVRQAPGQGLEWMGD
VNPNSGGSIYNQRFKGRFVFSLDTSVSMAYLQISSLKAEDTAVYYCARNL
GPSFYFDYWGQGTTLTVSS;

(SEQ ID NO: 43)
QVQLVQSGSELKKPGASVKVSCKASGFTFTDYTMNWVRQAPGQGLEWMGD
VNPNSGGSTYAQFTGRFVFSLDTSVSMAYLQISSLKAEDTAVYYCARNLG
PSFYFDYWGQGTTLTVSS;

(SEQ ID NO: 44)
QMQLVQSQPEVKKPGTSVKVSCKASGFTFTDYTMDWVRQARGQRLEWIGD

VNPNSGGSIYNQRFKGRVTITRDMSTSTAYMELSSLRSEDTAVYYCAANL

GPSFYFDYWGQGTTLTVSS;

(SEQ ID NO: 45)
QMQLVQSQPEVKKPGTSVKVSCKASGFTFTDYTMQWVRQARGQRLEWIGD

VNPNSGGSNYAQFQERVTITRDMSTSTAYMELSSLRSEDTAVYYCAANLG

PSFYFDYWGQGTTLTVSS;

(SEQ ID NO: 46)
QVQLVQSGAEVKKPGASVKVSCKVSGFTFTDYTMDWVRQAPGKGLEWMGD

VNPNSGGSIYNQRFKGRVTMTEDTSTDTAYMELSSLRSEDTAVYYCATNL

GPSFYFDYWGQGTTLTVSS;

(SEQ ID NO: 47)
QVQLVQSGAEVKKPGASVKVSCKVSGFTFTDYTMHWVRQAPGKGLEWMGD

VNPNSGGSIYAQKFQGRVTMTEDTSTDTAYMELSSLRSEDTAVYYCATNL

GPSFYFDYWGQGTTLTVSS;

(SEQ ID NO: 48)
QVQLVQSGAEVKKPGSSVKVSCKASGFTFTDYTMDWVRQAPGQGLEWMGD

VNPNSGGSIYNQRFKGRVTITADKSTSTAYMELSSLRSEDTAVYYCARNL

GPSFYFDYWGQGTTLTVSS;

(SEQ ID NO: 49)
QVQLVQSGAEVKKPGSSVKVSCKASGFTFTDYTISWVRQAPGQGLEWMGD

VNPNSGGSNYAQKFQGRVTITADKSTSTAYMELSSLRSEDTAVYYCARNL

GPSFYFDYWGQGTTLTVSS;

(SEQ ID NO: 50)
QVQLVQSGAEVKKPGASVKVSCKASGFTFTDYTMDWVRQAPGQRLEWMGD

VNPNSGGSIYNQRFKGRVTITRDTSASTAYMELSSLRSEDTAVYYCARNL

GPSFYFDYWGQGTTLTVSS;

(SEQ ID NO: 51)
QVQLVQSGAEVKKPGASVKVSCKASGFTFTDYTMHWVRQAPGQRLEWMGD

VNPNSGGSKYSQKFQGRVTITRDTSASTAYMELSSLRSEDTAVYYCARNL

GPSFYFDYWGQGTTLTVSS;

(SEQ ID NO: 52)
QVQLVQSGAEVKKPGASVKVSCKASGFTFTDYTMDWVRQAPGQGLEWMGD

VNPNSGGSIYNQRFKGRVTMTRDTSISTAYMELSRLRSDDTAVYYCARNL

GPSFYFDYWGQGTTLTVSS;

(SEQ ID NO: 53)
QVQLVQSGAEVKKPGASVKVSCKASGFTFTDYTMHWVRQAPGQGLEWMGD

VNPNSGGSNYAQKFQGRVTMTRDTSISTAYMELSRLRSDDTAVYYCARNL

GPSFYFDYWGQGTTLTVSS;

(SEQ ID NO: 54)
QVQLVQSGAEVKKPGASVKVSCKASGFTFTDYTMDWVRQATGQGLEWMGD

VNPNSGGSIYNQRFKGRVTMTRNTSISTAYMELSSLRSEDTAVYYCARNL

GPSFYFDYWGQGTTLTVSS;

(SEQ ID NO: 55)
QVQLVQSGAEVKKPGASVKVSCKASGFTFTDYTINWVRQATGQGLEWMGD

VNPNSGGSGYAQKFQGRVTMTRNTSISTAYMELSSLRSEDTAVYYCARNL

GPSFYFDYWGQGTTLTVSS;

(SEQ ID NO: 56)
QVQLVQSGAEVKKPGASVKVSCKASGFTFTDYTMDWVRQAPGQGLEWMGD

VNPNSGGSIYNQRFKGRVTMTRDTSTSTVYMELSSLRSEDTAVYYCARNL

GPSFYFDYWGQGTTLTVSS;

(SEQ ID NO: 57)
QVQLVQSGAEVKKPGASVKVSCKASGFTFTDYTMHWVRQAPGQGLEWMGD

VNPNSGGSSYAQKFQGRVTMTRDTSTSTVYMELSSLRSEDTAVYYCARNL

GPSFYFDYWGQGTTLTVSS.

In a preferred embodiment of the invention, the amino acid sequence of the heavy chain constant region of the anti-HER2 antibody is:

(SEQ ID NO: 58)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPG.

In a preferred embodiment of the invention, the structure of the antibody-drug conjugate is as shown in formula II:

Ab-(L-D)n     II wherein:

Ab is an antibody;

D is a small molecule drug that inhibits tumor cells;

L is a linker connecting the antibody and the drug;

In another preferred embodiment, n is from 1 to 8, preferably n is an integer.

In another preferred embodiment, the structure of D is as shown in formula III:

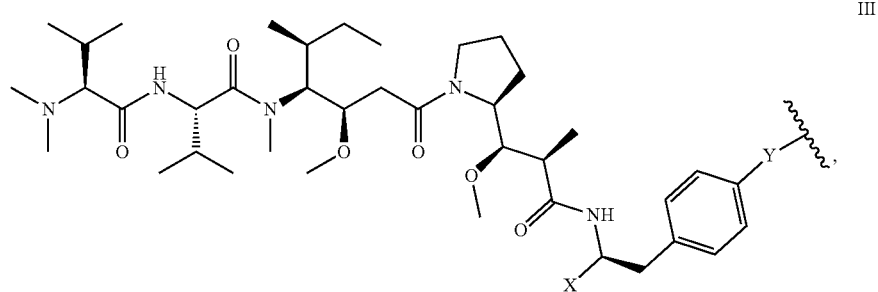

in formula III, Y is O or NH,
the wavy line indicates the connection position with L,
X is CH$_2$N$_3$ or

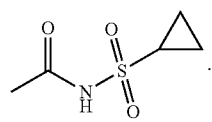

In a preferred embodiment of the invention, the structure of the antibody-drug conjugate is as shown in formula IV (that is, L includes L$^1$-L$^2$):

$$Ab\text{-}(L^1\text{-}L^2\text{-}D)_n,\qquad\text{IV}$$

in formula IV, the structure of L$^1$-L$^2$ is selected from

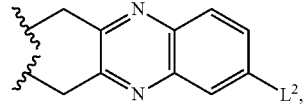 or

-continued

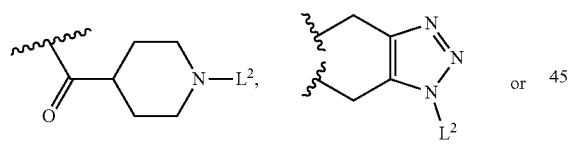

wherein L$^2$ is a linker selected from —(CH$_2$)n-, —(CH$_2$CH$_2$O)n-, Val-Cit, Ala-Ala-Asn, or a combination thereof;

Ab, D, n are as described above;

the wavy line indicates the connection position with antibody.

In another preferred embodiment, the antibody-drug conjugate is selected from: ZV0201, ZV0202, ZV0203, ZV0204, ZV0205, ZV0230, ZV0207, ZV0231, ZV0232 the structure of conjugate ZV0203 is shown as follows:

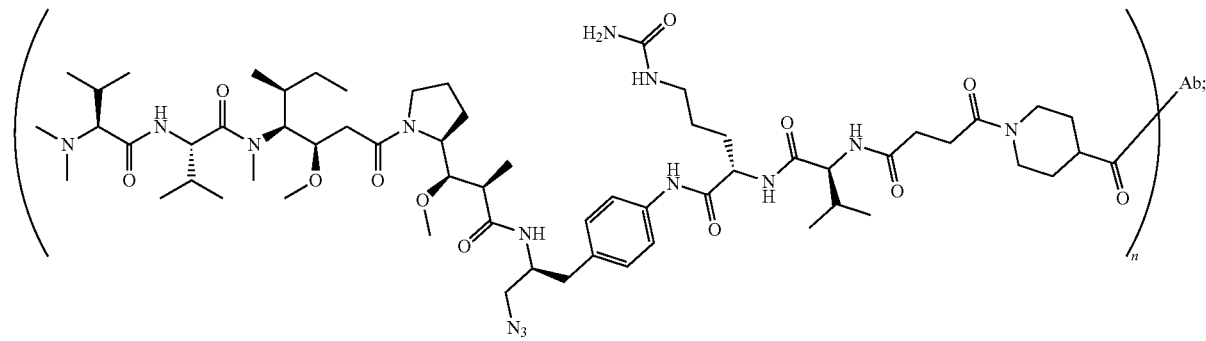

the structure of conjugate ZV0230 is shown as follows:
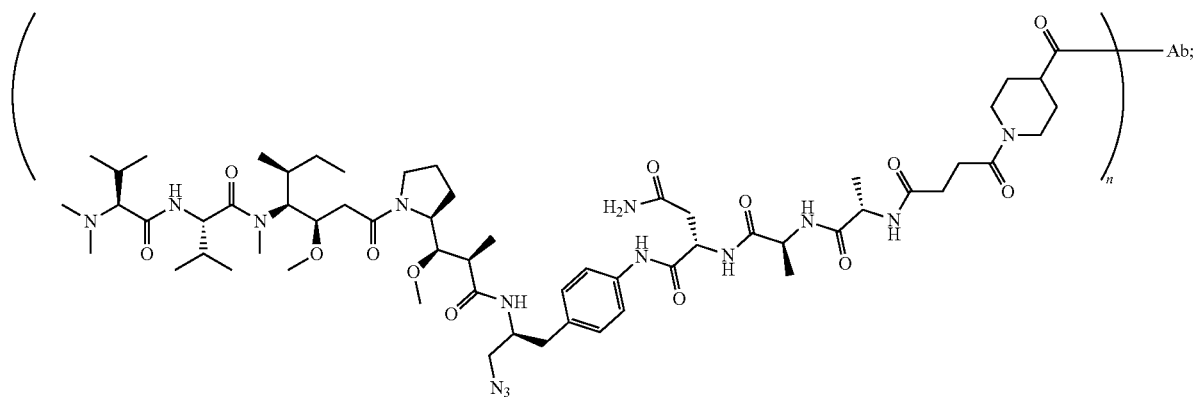
the structure of conjugate ZV0201 is shown as follows:
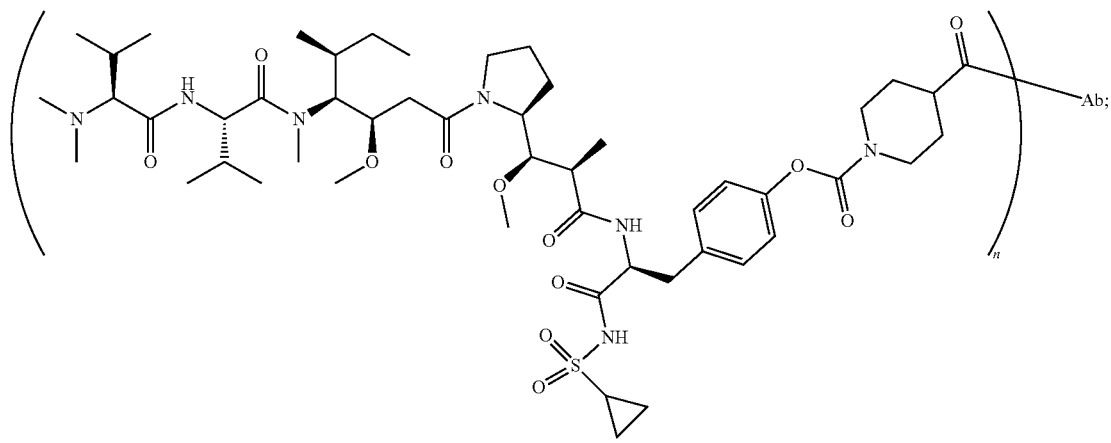
the structure of conjugate ZV0207 is shown as follows:
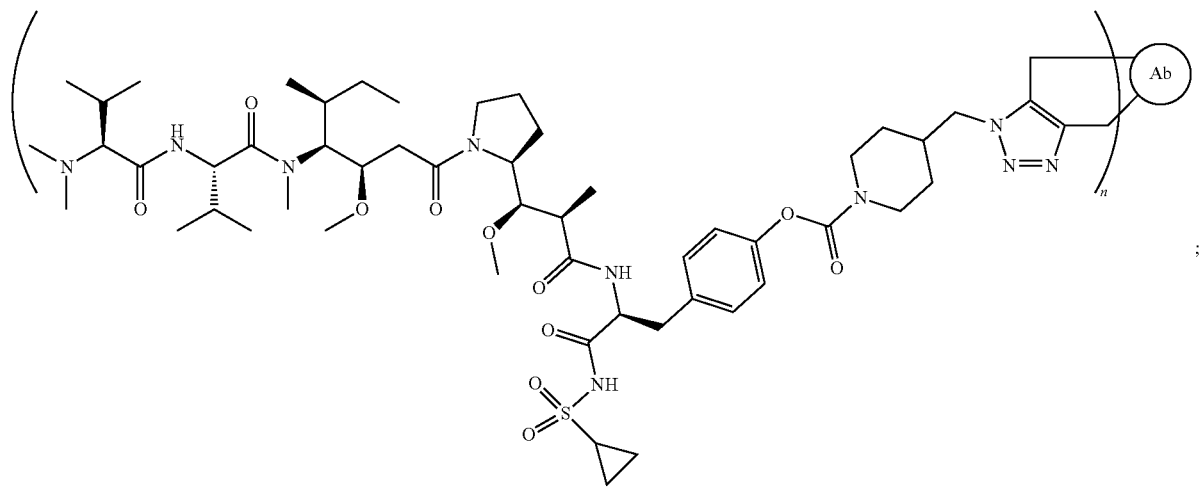

the structure of conjugate ZV0231 is shown as follows:
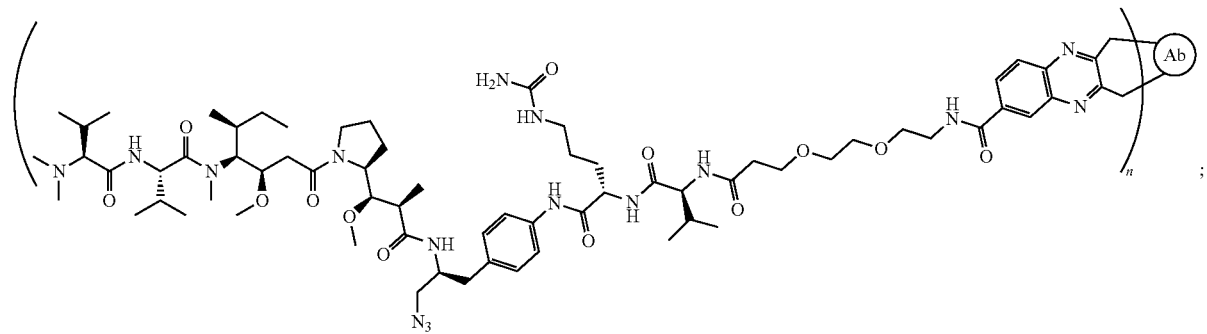
the structure of conjugate ZV0232 is shown as follows:
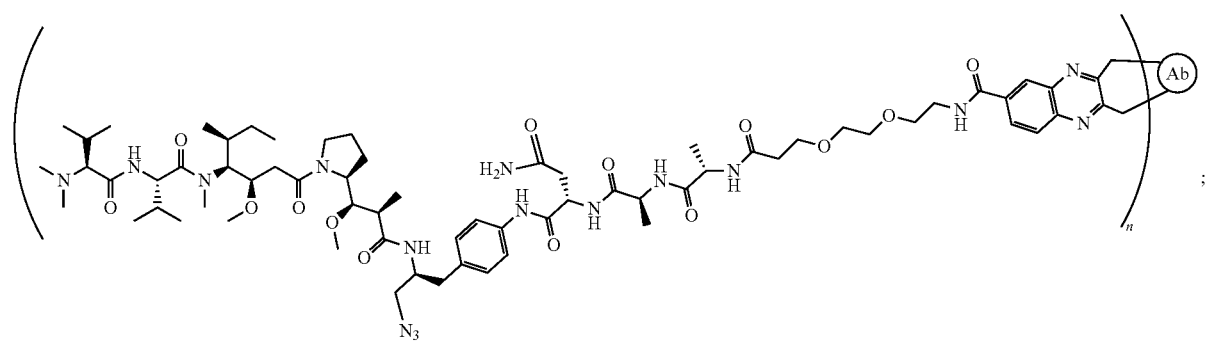
the structure of conjugate ZV0202 is shown as follows:
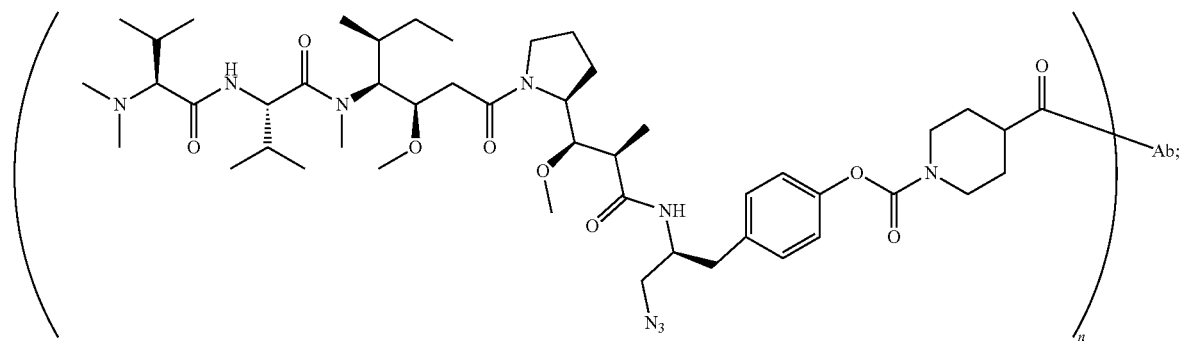

the structure of conjugate ZV0204 is shown as follows:

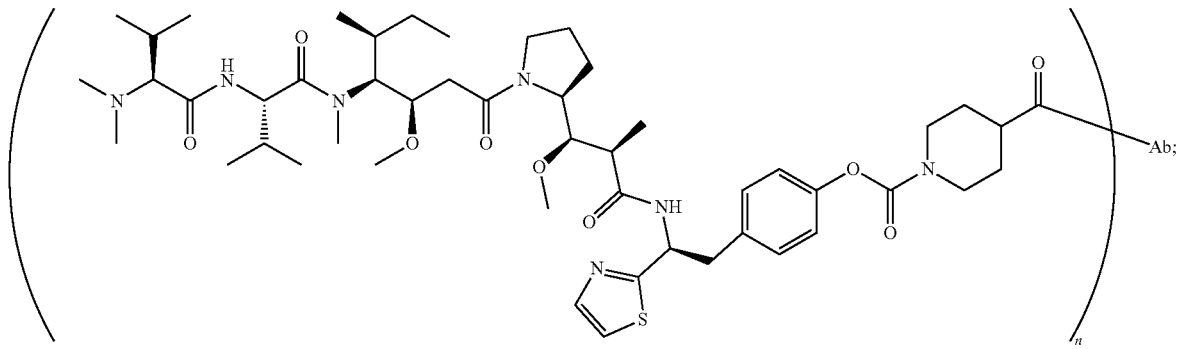

the structure of conjugate ZV0205 is shown as follows:

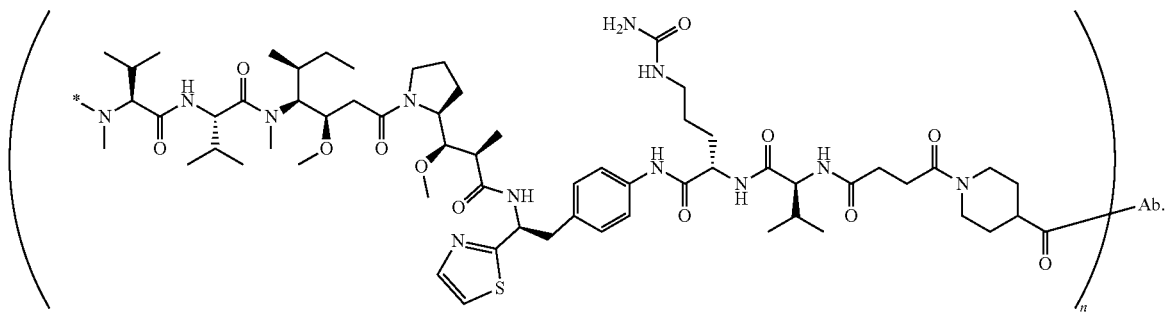

In another preferred embodiment, the anti-HER2 antibody is pertuzumab, and said pertuzumab includes Perjeta® and biosimilar thereof.

The coupling method for preparing the antibody-drug conjugate of the present invention includes two coupling modes of K-Lock and C-Lock. In the K-Lock coupling mode, the drug molecule is coupled to a lysine (K) residue in the antibody sequence, and in the C-Lock coupling mode, the drug molecule is coupled to a cysteine (C) residue in the antibody sequence. The coupling method of the antibody-drug conjugate of the present invention is summarized below.

K-Lock method: The antibody can be directly linked to L1-D in a mild solution system. For example, 6-10 fold excess of L1-D reacts with antibody for 3-16 h at room temperature. Excess small molecule L1-D is removed by ultrafiltration. The antibody-drug conjugates are loaded onto a hydrophobic chromatography column (HIC), and anti-HER2 antibody-drug conjugates with a coupling number of 2 are purified and obtained.

C-Lock method: After TCEP reduction, the antibody is directly linked to L2-D in a mild solution system. For example, the antibody is reduced with a 5-10 fold excess of TCEP at room temperature and excess TCEP is removed by ultrafiltration. 5-10 fold of L2-D is added to the reduced antibody solution for reaction, and excess small molecule L2-D is removed by ultrafiltration. The antibody-drug conjugates are loaded onto a hydrophobic chromatography column (HIC), and anti-HER2 antibody-drug conjugates with a coupling number of 4 are purified and obtained.

A plurality of antibody-K-Lock-Dolastatin derivatives and antibody-C-Lock-Dolastatin derivative conjugates are provided in the present invention, which are constituted by coupling Dolastatin derivative to antibody by K-Lock or C-Lock method. Preferably, the drug in the antibody-drug conjugate may comprise one or more compounds prepared in the examples of the present invention.

Use of the antibody-drug conjugate in the preparation of anti-tumor drugs is also provided in the present invention.

The anti-tumor drug comprises an effective amount of the antibody-drug conjugate according to the present invention, and at least one pharmaceutically acceptable carrier, diluent or excipient. For preparation, the active ingredient is usually mixed with an excipient, or diluted with an excipient, or enclosed in a carrier which may be in the form of capsule or sachet. When the excipient acts as a diluent, solid, semi-solid or liquid materials can be used as media for an excipient, carrier and ingredient. Thus, the composition may be a tablet, a pill, a powder, a solution, a syrup, a sterile injectable solution or the like.

Suitable excipients include lactose, glucose, sucrose, sorbitol, mannitol, starch, microcrystalline cellulose, polyvinylpyrrolidone, cellulose, water, and the like; preparations may also include wetting agent, emulsifier, preservative (such as methyl and propyl hydroxybenzoate), sweetener, and the like. The anti-tumor drug can be formulated in a unit or multi-dose form, each dosage form comprises calculated predetermined amount of the anti-her2 antibody- Dolastatin conjugate to produce desired therapeutic effect, as well as suitable pharmaceutical excipients.

The anti-tumor drug can be administered by conventional routes including, but not limited to, intramuscular, intraperitoneal, intravenous, subcutaneous, intradermal, topical administration and the like.

When the drug is used, a safe and effective amount of the antibody-drug conjugate is administered to a human wherein the safe effective amount is preferably in the range of 0.5 to 50 micrograms per kilogram of body weight, more preferably in the range of 1 to 10 micrograms per kilogram of body weight. Of course, the route of administration, the patient's health status and other factors, should be considered for the specific dose, which are within the scope of skills of skilled practitioners.

In addition, the conjugates of the present invention may also be used in combination with other therapeutic agents, including but not limited to: various cytokines such as TNF, IFN, IL-2, etc.; various tumor chemotherapy drugs, such as 5-FU, methotrexate and other drugs that affect nucleic acid biosynthesis; alkylating agents such as nitrogen mustard and cyclophosphamide; drugs such as doxorubicin and actinomycin D that interfere with transcriptional processes to prevent RNA synthesis; drugs such as vincristine, camptothecin classes etc. that affect protein synthesis and certain hormone drugs, and so on.

Compared with prior arts, the beneficial effects of the present invention are:

(1) In the present invention, site-directed and quantitative coupling of antibody and drug are obtained via simple chemical and purification steps without changing the antibody-expressing cell strain;

(2) The antibody-drug conjugate according to the present invention has significantly better activity when the drug is coupled to the constant region of the light chain of the antibody, and is easy to prepare with high yield, and is suitable for large-scale production;

(3) The conjugate of the present invention has both of the biological functions of anti-her2 antibody and dolastatin. It has the ability of anti-her2 antibody to kill tumor cells, and the ability of dolastatin to inhibit tubulin in cells thereby inducing apoptosis. With the synergy of the both, the anti-tumor effect is significantly enhanced;

(4) The conjugate of the present invention specifically binds to the her2 receptor on the surface of tumor cells via anti-her2 antibody, and Dolastatin is directly transported to tumor cells, and is released and works in tumor cells, thereby killing her2 positive tumor cells and reducing toxic side effects caused by the administration of toxin molecules alone.

(5) The antibody-drug conjugate prepared by the method of the present invention has an average number of coupled drug molecules of about 2, and the process is stable. The amount of the coupled drug can be saved, thereby saving the preparation cost.

(6) Use of the specific linker screened in the present invention to link anti-her2 antibody and drug not only makes the antibody-drug conjugate easy to prepare with high yield, but still retains the targeting activity of the antibody.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by US Sambrook et al., Molecular Cloning Laboratory Guide (New York: Cold Spring Harbor Laboratory Press, 1989), or according to the manufacture's instructions. Unless indicated otherwise, all percentage and parts are calculated by weight. Unless otherwise stated, the experimental materials and reagents used in the following examples are available from commercially available sources.

General Synthesis Step a Method for Synthesizing an Active Ester from a Compound Having a Carboxyl Group (Such as NHS)

A carboxyl compound was dissolved in dichloromethane or N, N-dimethylformamide, 1.5 equivalents of N-hydroxysuccinimide, 1.5 equivalents of EDCI were added. The reaction solution was stirred at room temperature for 1 h until most of the carboxyl compound was consumed. The progress of the reaction was monitored by RP-HPLC. The reaction solution was then diluted with dichloromethane, and organic phase was washed with citric acid (aq. 10%) and saturated brine. The organic phase was separated and dried, and purified by HPLC or medium pressure normal phase silica gel chromatography, so as to give the corresponding active ester.

Example 1 Synthesis of Compound 7

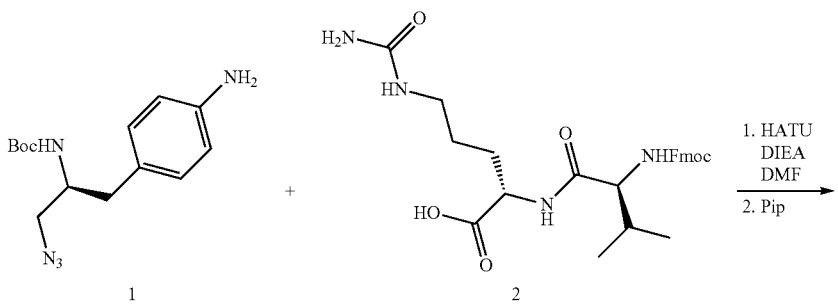

-continued
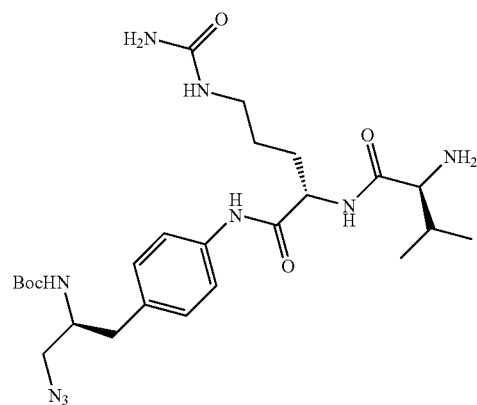
3
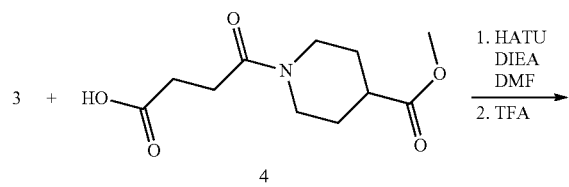
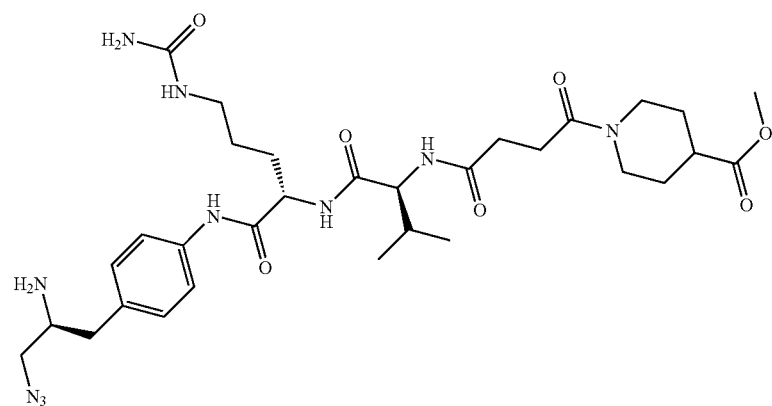
5
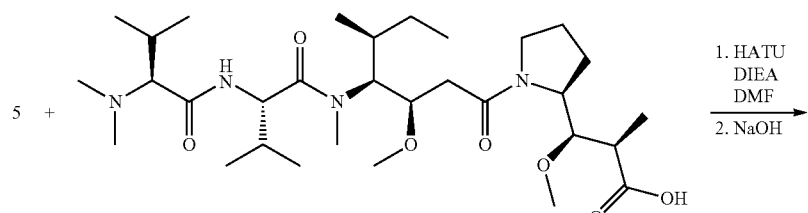

-continued

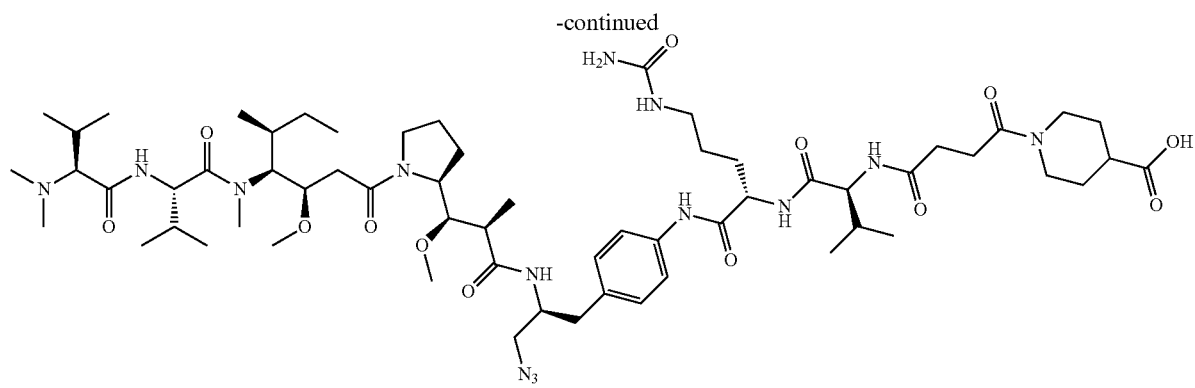

7

Synthesis of Compound 3

Compound 2 (261 mg, 0.52 mmol) was dissolved in 6 mL of DMF. Then HATU (217 mg, 0.57 mmol), DIEA (362 μL, 2.08 mmol), and amino compound 1 (213 mg, 0.52 mmol) were added. After stirred for 30 min, then 400 μL piperidine was added and stirred for another 10 min. The reaction solution was concentrated and directly purified by HPLC to obtain compound 3 (171 mg, 60%). MS m/z 548.3 (M+H).

Compound 5

Compound 4 (37 mg, 0.15 mmol) was dissolved in 4 mL of DMF. Then HATU (59 mg, 0.15 mmol), DIEA (108 μL, 0.6 mmol), and amino compound 3 (102 mg, 0.15 mmol) were added. The reaction solution was stirred for 30 min, then evaporated to dryness under reduced pressure and then dissolved in 2 mL of dichloromethane. 1 mL of TFA was added and stirred for 10 min. The reaction solution was evaporated to dryness under reduced pressure and purified by HPLC to obtain compound 5 (94 mg, 78%). MS m/z 673.4 (M+H).

Synthesis of Compound 7

Compound 6 (85 mg, 0.12 mmol) was dissolved in 2 mL of DMF. Then HATU (48 mg, 0.12 mmol), DIEA (83 μL, 0.48 mmol), and amino compound 5 (94 mg, 0.12 mmol) were added. The reaction solution was stirred for 30 min. Then 90 mg of NaOH in 1 mL aqueous solution was added and stirred for 30 min. The reaction solution was evaporated to dryness in vacuo and then directly purified by HPLC to obtain compound 7 (86 mg, 58%). MS m/z 1239.7 (M+H).

Example 2 Synthesis of Compound 11

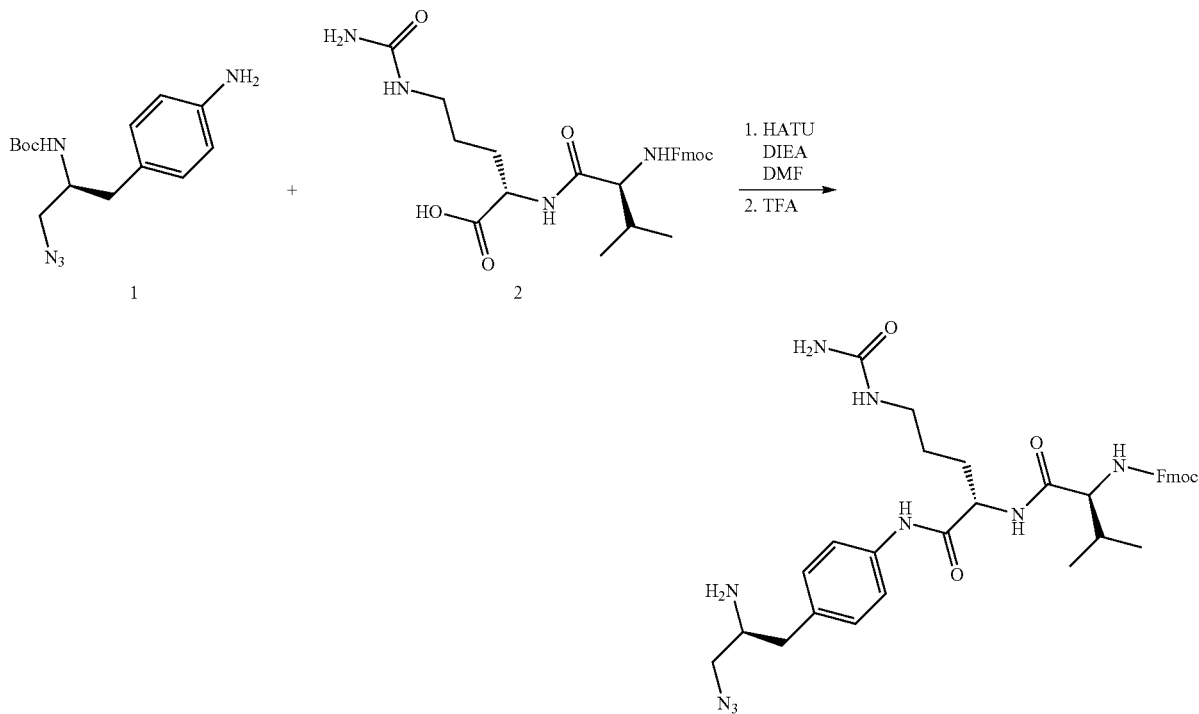

8

-continued

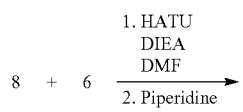

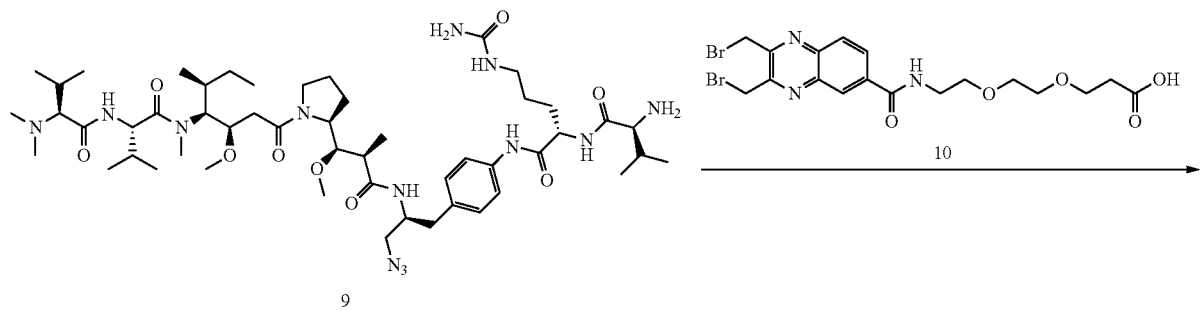

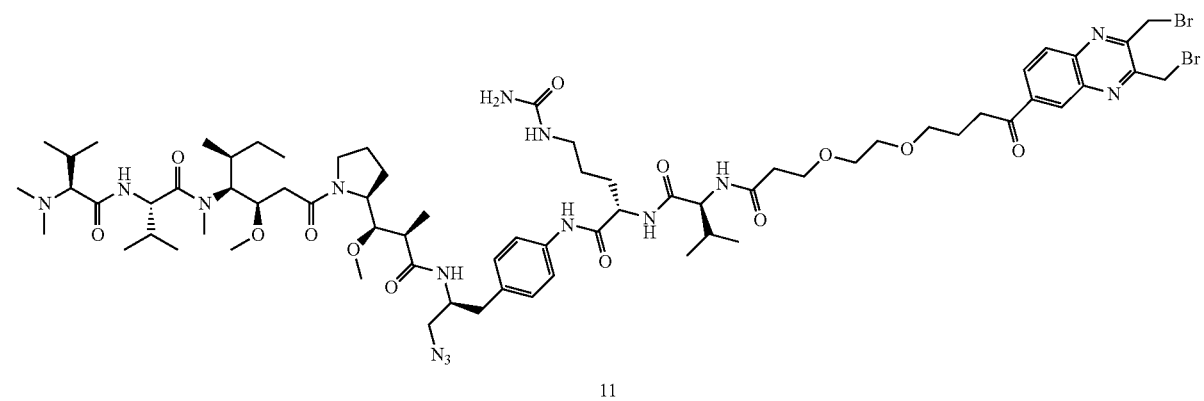

Compound 2 (130 mg, 0.26 mmol) was dissolved in 3 mL of DMF. Then HATU (110 mg, 0.29 mmol), DIEA (175 μL, 1 mmol), and amino compound 1 (110 mg, 0.27 mmol) were added. The reaction solution was stirred for 30 min, and evaporated to dryness in vacuo. The residue was dissolved in TFA/dichloromethane (1/4, v/v, 5 mL) and stirred for 30 min. The reaction solution was evaporated to dryness under reduced pressure and purified by HPLC to obtain compound 8 (108 mg, 65%). MS m/z 670.5 (M+H).

Compound 6 (85 mg, 0.12 mmol) was dissolved in 2 mL of DMF. Then HATU (48 mg, 0.12 mmol), DIEA (83 μL, 0.48 mmol), and amino compound 8 (94 mg, 0.12 mmol) were added. The reaction solution was stirred for 30 min, and then 0.2 mL piperidine was added and stirred for 30 min. The reaction solution was concentrated and purified by HPLC to obtain compound 9 (87 mg, 63%). MS m/z 1028 (M+H).

PyBrop (0.055 mmol) and DIEA (35 μL) were added to the solution of compound 9 (57 mg, 0.05 mmol) and carboxyl compound 10 (27 mg) in dichloromethane/DMF (3/1, v/v, 4 mL). The reaction solution was stirred for 30 min and concentrated. The residue was purified by HPLC to obtain compound 11 (41 mg). MS m/z 1529.7 (M+H).

Example 3 Synthesis of Compound 16

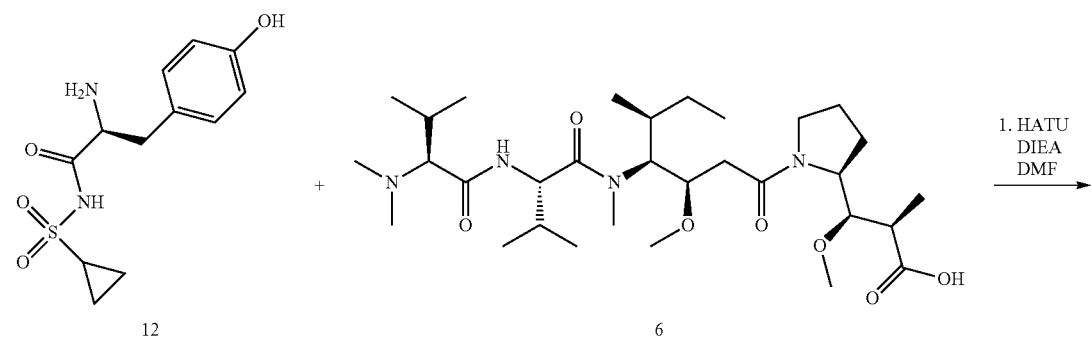

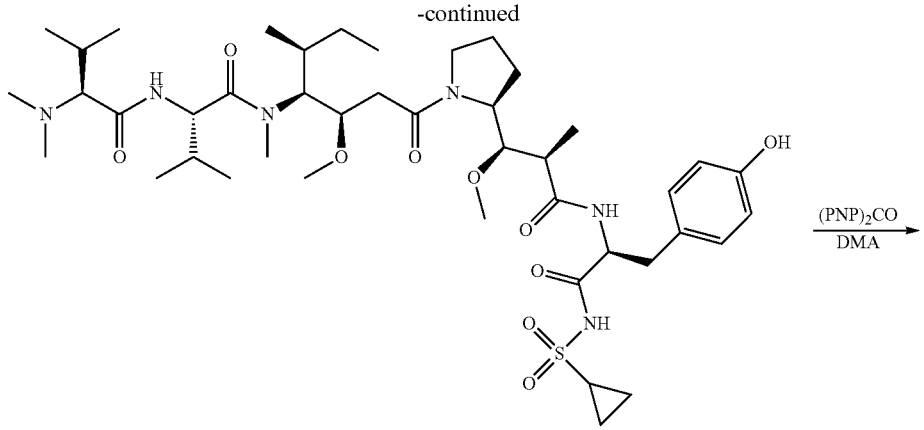

13

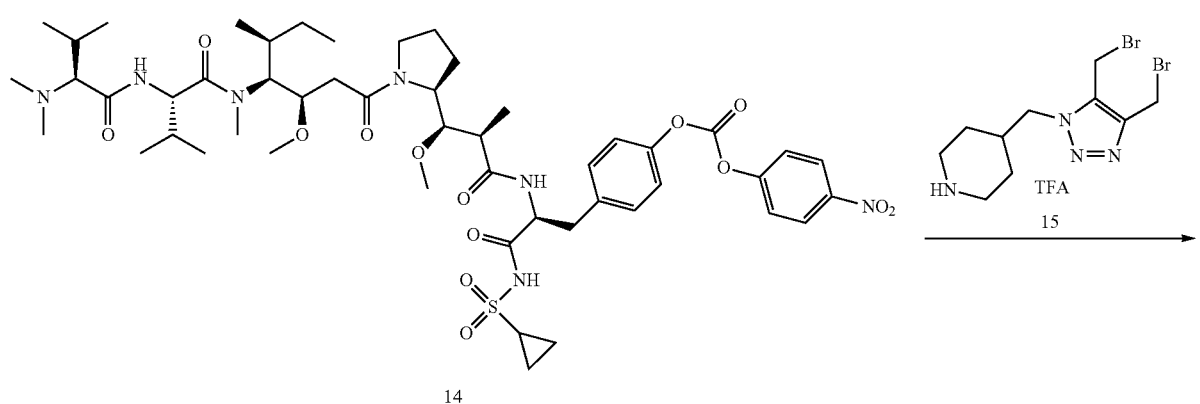

14

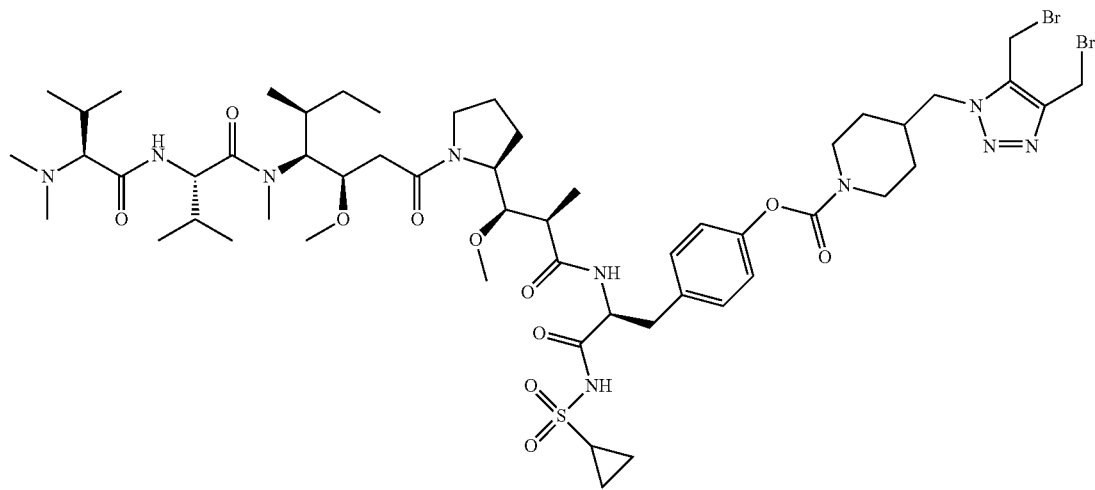

16

Compound 13

Compound 6 (1000 mg, 1.67 mmol) was dissolved in 20 mL of DMF. Then HATU (640 mg, 1.68 mmol), DIEA (870 μL, 5.00 mmol), and amino compound 12 (535 mg, 1.67 mmol) were added. The reaction solution was stirred for 30 min. The reaction solution was concentrated to dryness and purified by HPLC to obtain compound 13 (1140 mg, 70%). MS m/z 865.5 (M+H).

Compound 14

Compound 13 (500 mg, 0.57 mmol) was dissolved in 10 mL of DMA, Then Di (p-nitrophenyl) carbonate (210 mg, 0.69 mmol) and DIEA (35 μL, 0.2 mmol) were added. The reaction solution was stirred for 18 h, then 100 mL of diethyl ether was added and solids precipitated. The precipitate was collected and dried to obtain compound 14 (500 mg, 85%). MS m/z 1030.6 (M+H).

Compound 16

The Compound 15 (0.15 mmol, 67 mg) in acetonitrile/water (1/1, v/v, 1 mL) was added to the solution of Compound 14 (0.1 mmol) in tetrahydrofuran (3 mL), then DIEA (50 μL) was added. The reaction solution was stirred for 30 min and then acidified and concentrated. The residue was purified by HPLC to obtain compound 16 in white solid (87 mg). MS m/z 1243.6 [M+H]$^+$.

Example 4 Synthesis of Compound 18

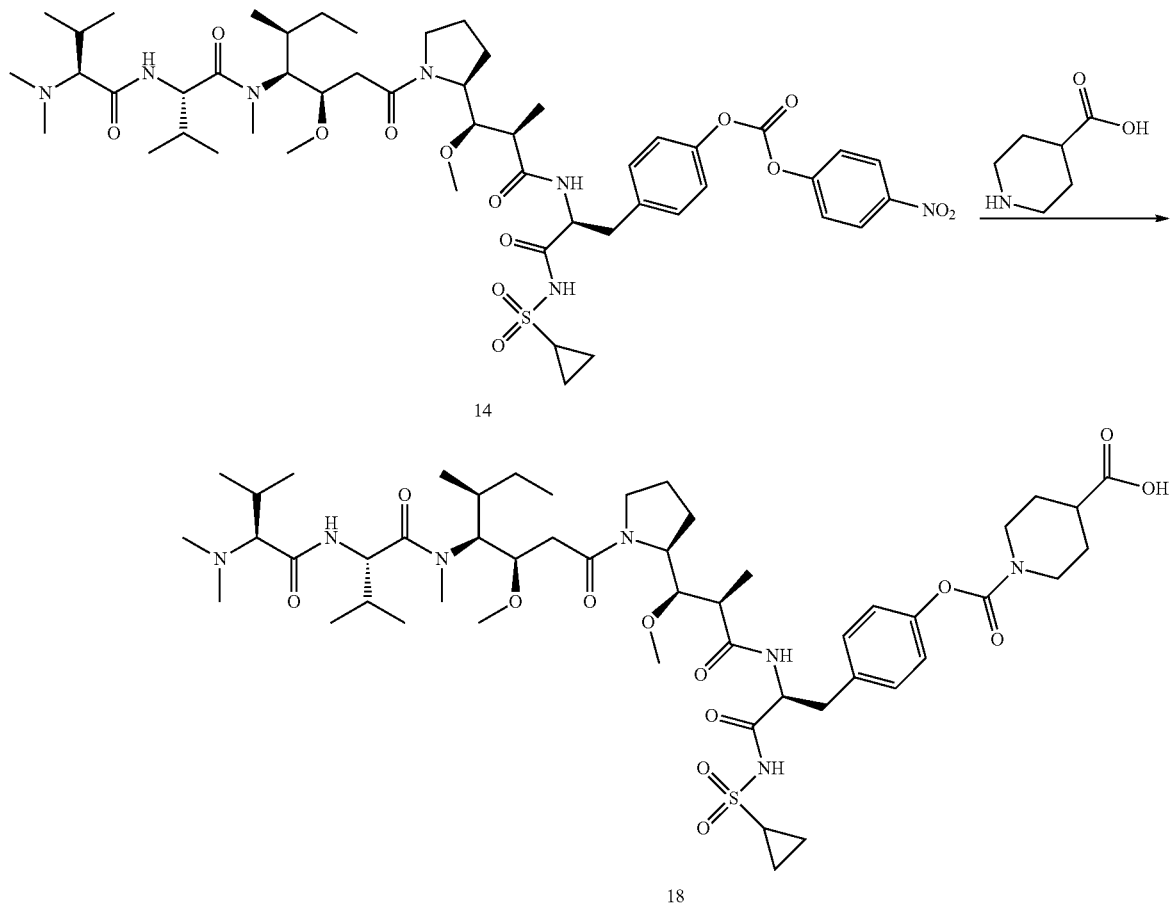

Compound 14 (0.1 mmol) was dissolved in 3 mL of tetrahydrofuran. Then piperidine-4-carboxylic acid (60 mg) and saturated aqueous NaHCO$_3$ (1 mL) were added. The reaction solution was stirred at room temperature for 30 min, then pH was adjusted to 4-5 by using 1 N HCl. The reaction solution was concentrated and purified by HPLC to obtain compound 18 (68 mg). MS m/z 1020.7 (M+H).

Example 5 Synthesis of Compound 23

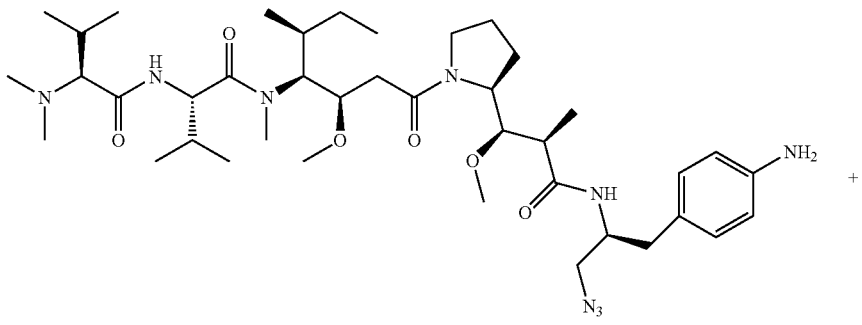

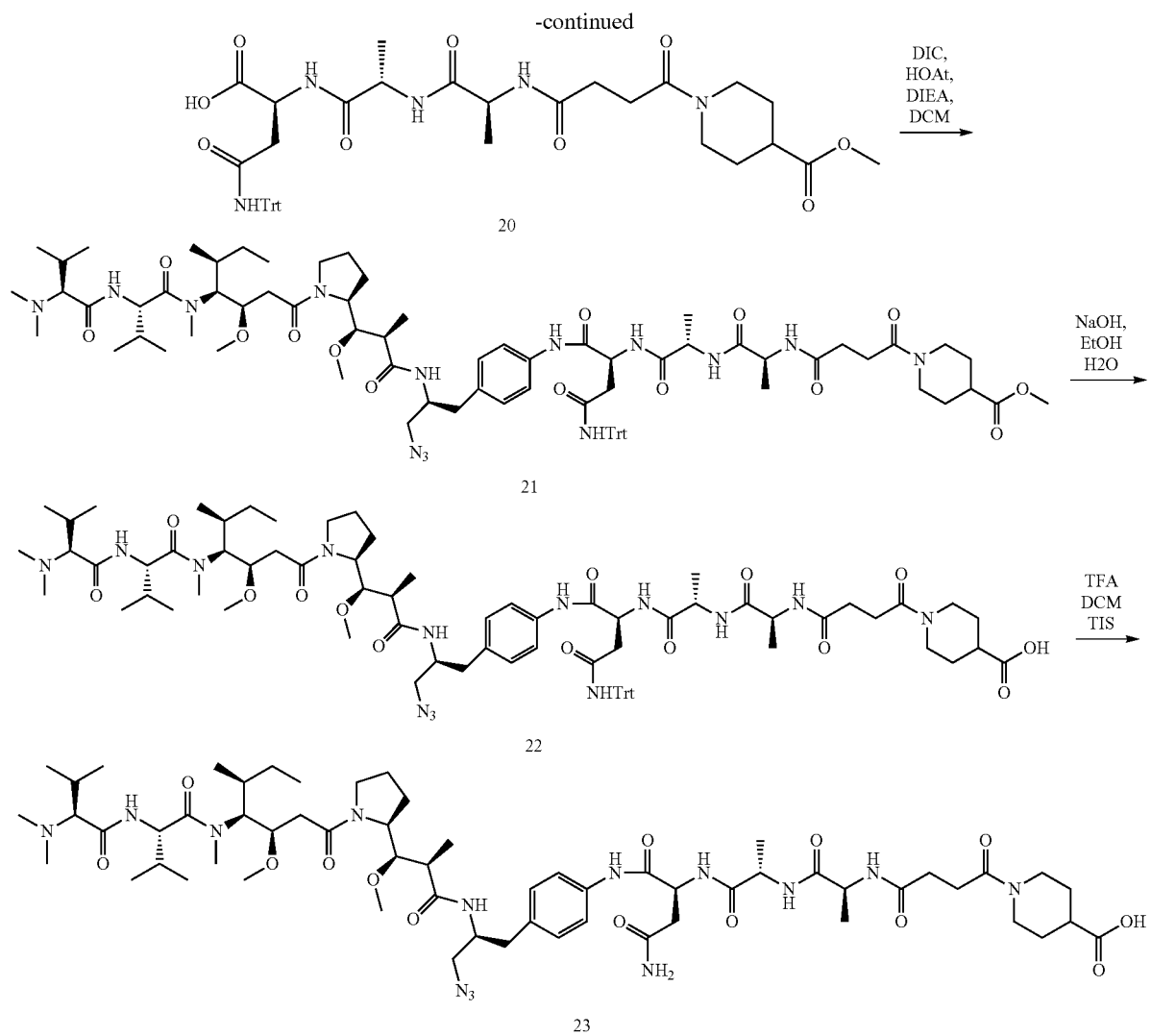

Synthesis of Compound 21

TFA salt of Compound 19 (1 mmol), Compound 20 (1 eq.), HOAt (3 eq.), dichloromethane (20 mL), DIEA (6 eq.), and DIC (2 eq.) were added to a round bottom flask and stirred for 16 h. Then the reaction solution was diluted by 20 mL dichloromethane and washed by water. The organic layer was evaporated to dryness in vacuo to obtain compound 3, which is directly used in the next step. MS m/z 1496.5 (M+H).

Synthesis of Compound 22

Compound 21 (1 mmol), 20 mL of ethanol and 2M NaOH aqueous solution were added to a round bottom flask and stirred for 3 h. The reaction solution was adjusted to neutrality with acetic acid and purified by HPLC to obtain compound 22. MS m/z 1482.3 (M+H).

Synthesis of Compound 23

Compound 22 (0.5 mmol) was dissolved in 10 mL of dichloromethane, 10 mL of TFA and 1 mL of triisopropylsilane and stirred for 1 h. The reaction solution was concentrated and purified by HPLC to obtain compound 23. MS m/z 1239.8 (M+H).

Example 6 Synthesis of Compound 27

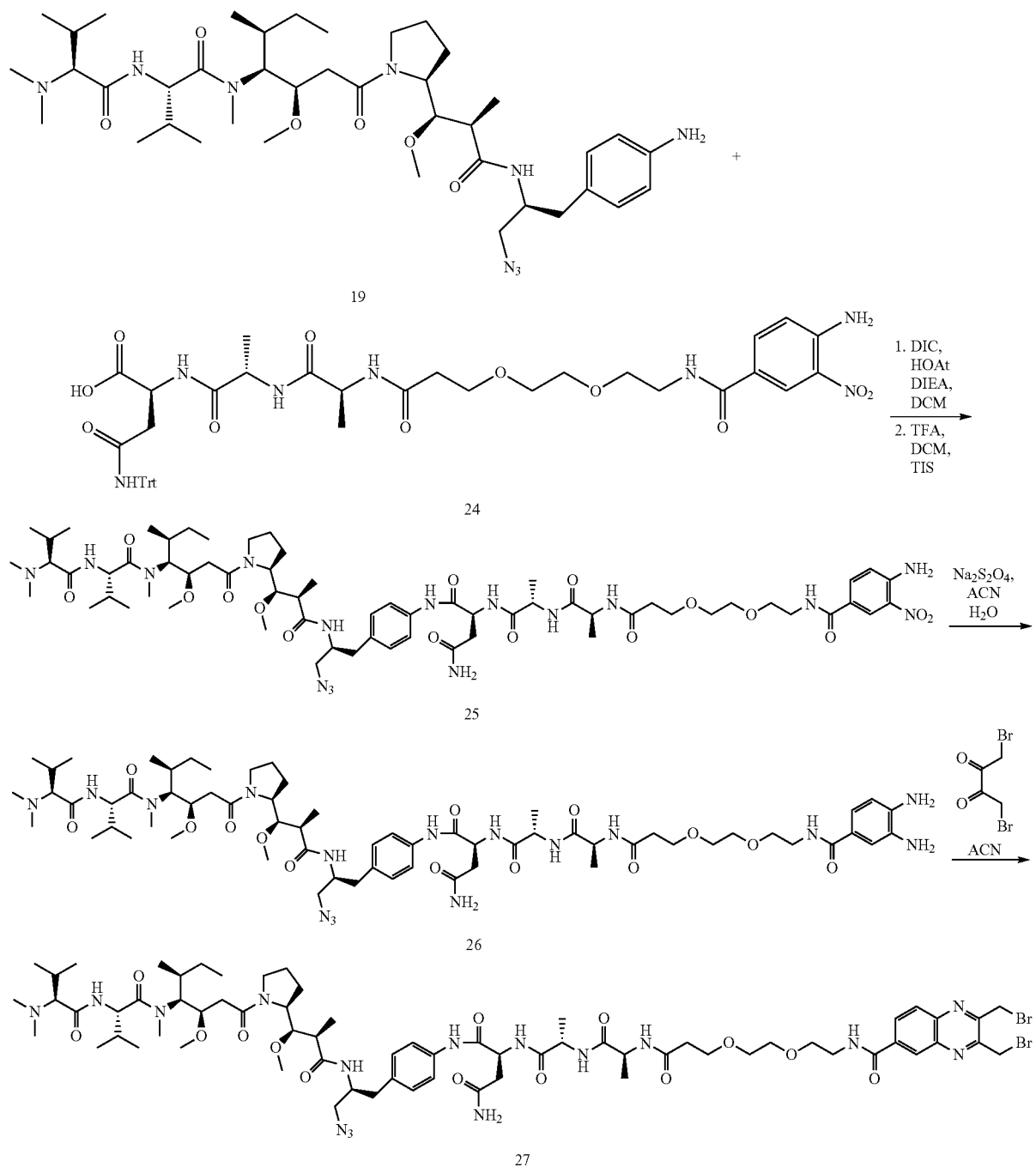

Synthesis of Compound 5

TFA salt of Compound 19 (1 mmol), Compound 24 (1 eq.), HOAt (3 eq.), dichloromethane (20 mL), DIEA (6 eq.), and DIC (2 eq.) were added to a round bottom flask. The reaction solution was stirred for 16 h, then diluted by 20 mL dichloromethane, washed with 20 mL water, and evaporated to dryness under reduced pressure to obtain glassy solid which was directly used in the next step. The obtained solid was dissolved in 10 mL of dichloromethane, 10 mL of TFA and 1 mL of triisopropylsilane and stirred for 1 h. The reaction solution was evaporated to dryness under reduced pressure and purified by HPLC to obtain compound 6. MS m/z 1351.5 (M+H).

Synthesis of Compound 26

Compound 25 (0.5 mmol) was dissolved in 20 mL of acetonitrile, 5 mL of water and 10 mL saturated $NaHCO_3$ aqueous solution, then $Na_2SO_4$ (4 eq.) was added and stirred for 20 min. The reaction solution was concentrated and purified by HPLC to obtain compound 7. MS m/z 1321.7 (M+H).

Synthesis of Compound 27

Compound 26 was dissolved in 10 mL of acetonitrile and 1,4-Dibromo-2,3-butanedione (3 eq.) was added. The reaction solution was stirred for 20 min and purified by HPLC to obtain compound 27. MS m/z 1527.6 (M+H).

Example 7 Preparation of Compound 30

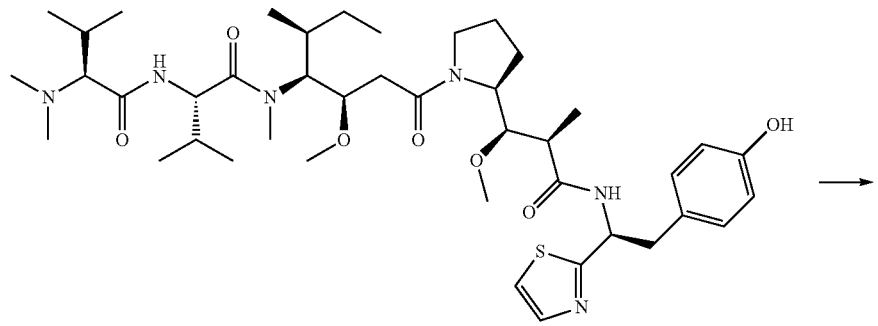
28

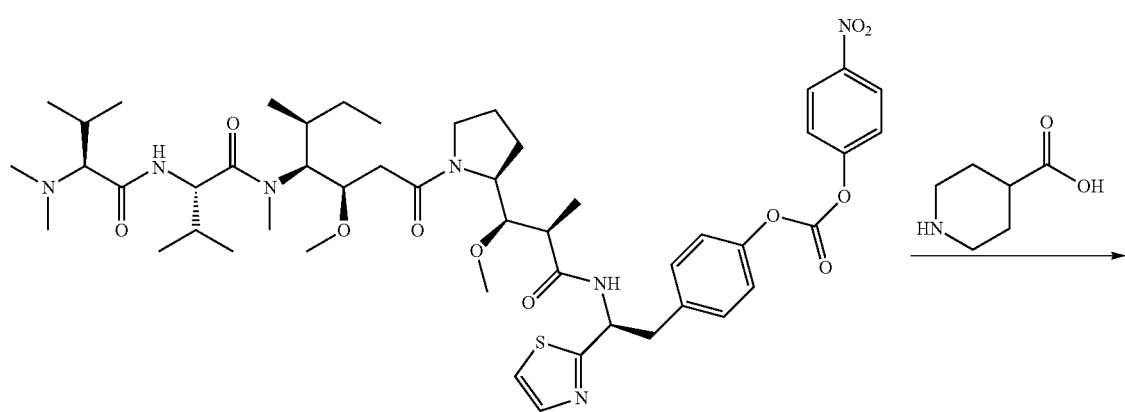
29

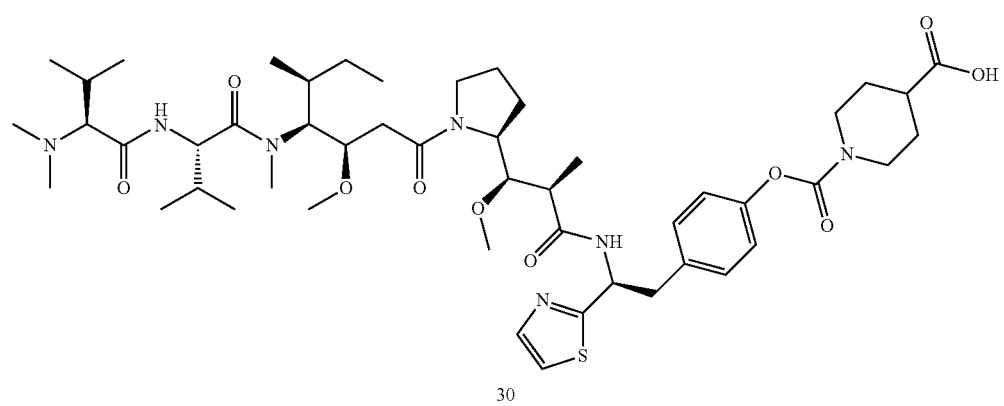
30

Compound 29 was prepared from Compound 28 (0.2 mmol) in the same manner as Compound 14. Using the method of synthesizing compound 18, Compound 29 reacted with piperidine 4-carboxylic acid, and compound 30 (117 mg) in white powder was obtained via purification by HPLC. MS m/z 956.7 (M+H).

Example 8 Preparation of Compound 33
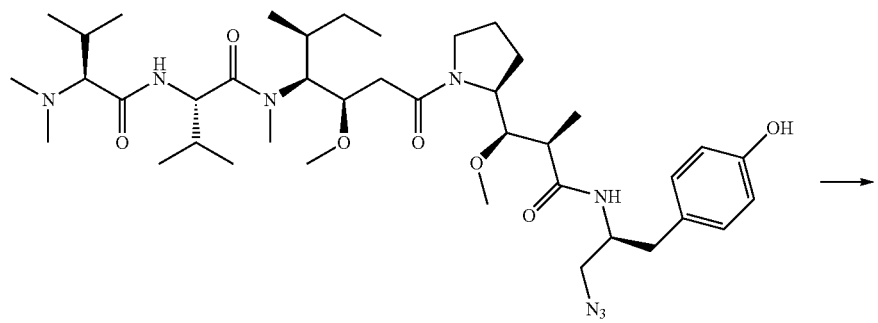
31
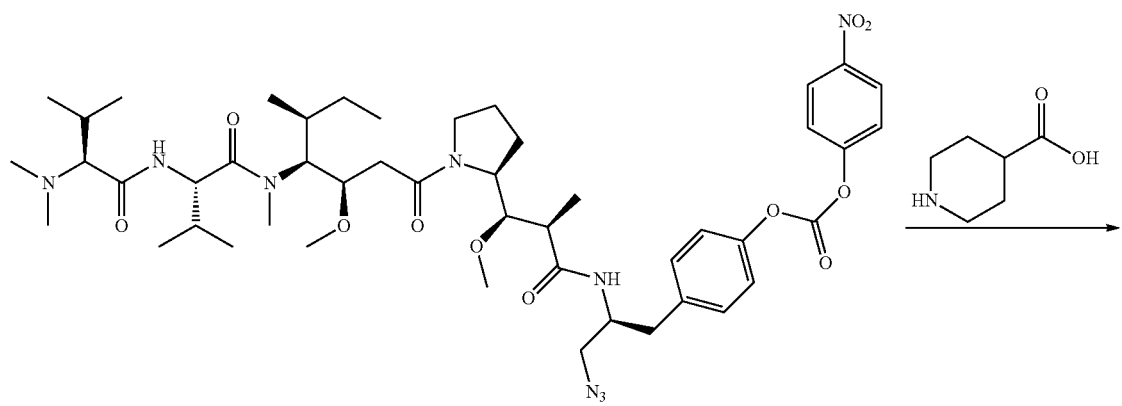
32
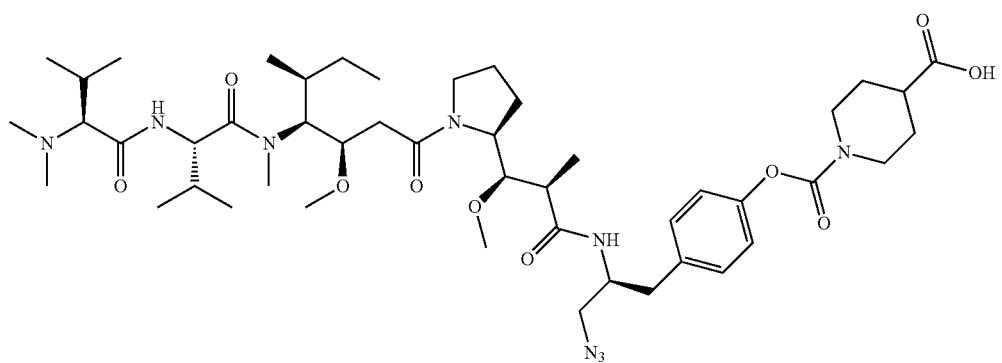
33
Compound 32 was prepared from Compound 31 (0.2 mmol) in the same manner as Compound 14. Using the method of synthesizing compound 18, Compound 29 reacted with piperidine 4-carboxylic acid, and compound 33 (109 mg) in white powder was obtained via purification by HPLC. MS m/z 928.6 (M+H).

Example 9 Preparation of Compound 37
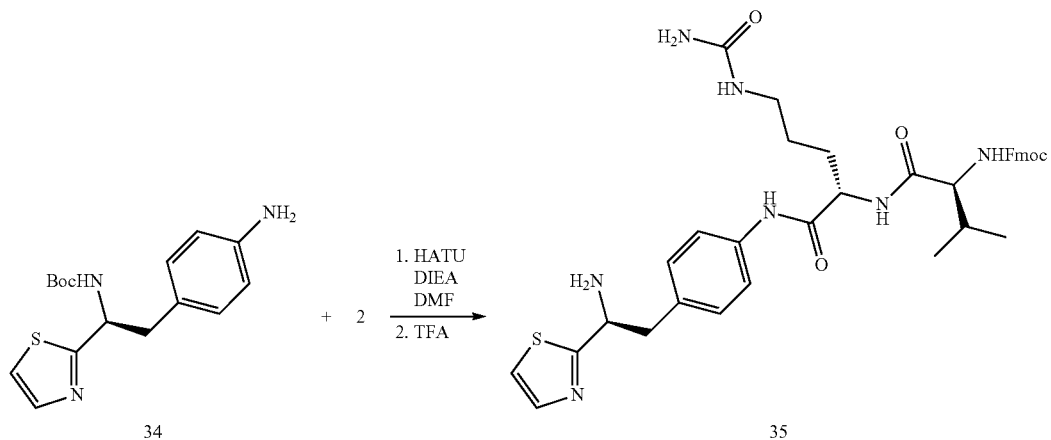
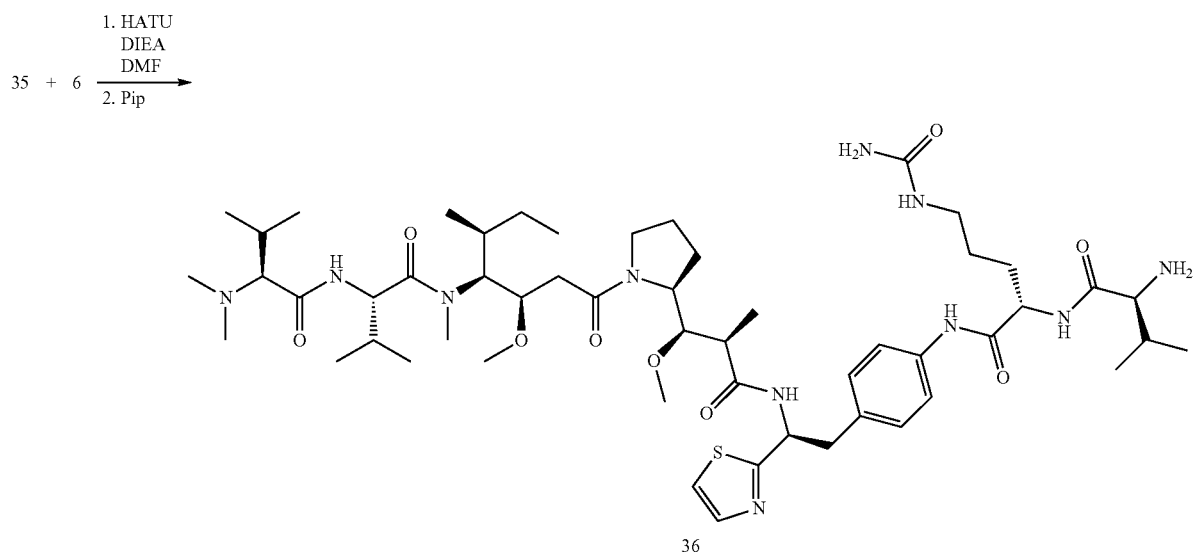
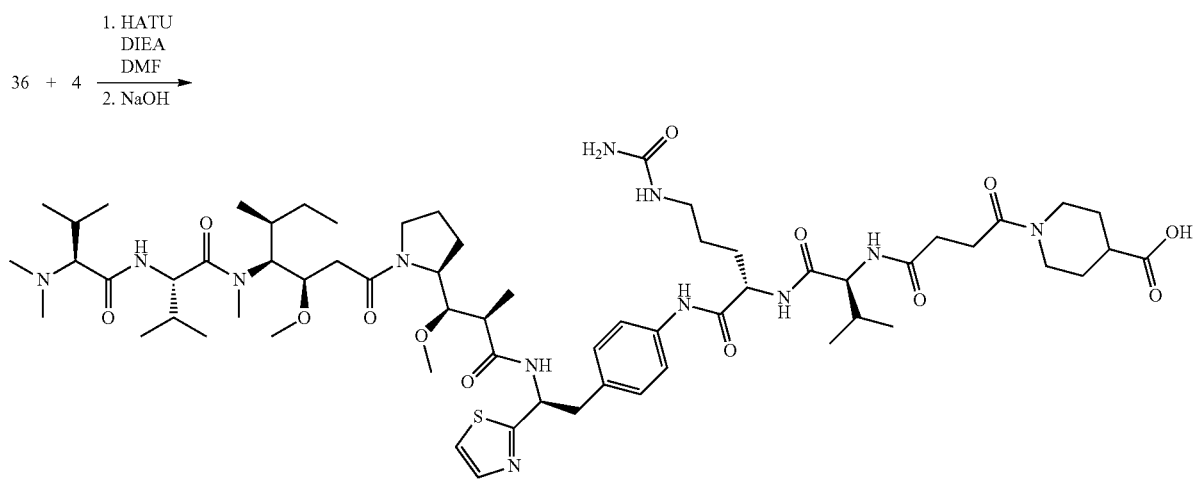

Preparation of Compound 35

HATU (110 mg, 0.29 mmol), DIEA (181 μL, 1.04 mmol) and Compound 34 (83 mg, 0.26 mmol) were added to the solution of Compound 2 (131 mg, 0.26 mmol dissolved in 4 mL DMF) in turn. After stirred for 30 min, the solution was evaporated under vacuum. The residue was dissolved in 2 mL of DCM and then 1 mL of TFA was added and stirred for 10 min. The solution was evaporated under vacuum and purified by HPLC to obtain Compound 35 (118 mg, 67%). MS m/z 698.4 (M+H).

Preparation of Compound 36

HATU (68 mg, 0.17 mmol), DIEA (118 μL, 0.68 mmol) and Compound 35 (118 mg, 0.17 mmol) were added to the solution of Compound 6 (125 mg, 0.17 mmol dissolved in 4 mL DMF) in turn. After stirred for 30 min, 400 L of piperidine was added and stirred for another 10 min. The solution was evaporated under vacuum and purified by HPLC to obtain Compound 36 (196 mg, 87%). MS m/z 1056.6 (M+H).

Preparation of Compound 37

HATU (27 mg, 0.072 mmol), DIEA (50 μL, 0.288 mmol) and Compound 36 (85 mg, 0.067 mmol) were added to the solution of Compound 4 (17 mg, 0.72 mmol dissolved in 2 mL DMF) in turn. After stirred for 30 min, 1 mL of NaOH aqueous solution (1M) was added and stirred for another 60 min. Compound 37 (76 mg, 91%) was obtained by HPLC purification. MS m/z 1267.7 (M+H).

Example 10 Preparation of Anti-HER2 Antibody-Drug Conjugate

The K-Lock method was adopted (taking ZV0201 as an example): an antibody (such as that having the light chain variable region as shown in SEQ ID NO:1 and the light chain constant region as shown in SEQ ID NO:29 and the heavy chain variable region as shown in SEQ ID NO:58 and the heavy chain constant region as shown in SEQ ID NO:4) can be directly connected to L-D in a mild solution system. At room temperature 25° C. (range can be 4-37° C.), into 10 mg/ml of antibody (dissolved in phosphate buffer PBS, concentration range 5-30 mg/ml) 6-10 fold molar amount of L-D (dissolved in DMA and the volume does not exceed 10% of PBS) was added, and incubated for 3-16 h, and excess small molecule L-D was removed by ultrafiltration. The antibody-drug conjugates were loaded onto a hydrophobic chromatography column (HIC), equilibrated with 0.75-1M ammonium sulfate solution, and then eluted with 25 mM ammonium sulfate solution. The eluates with coupling number of 2 were combined, PBS was used for replacement and anti-HER2 antibody-drug conjugates with coupling number of 2 were obtained.

The inventors have found that pH has a significant effect on the coupling reaction during the coupling of antibody and the drug. Preferably, the pH of coupling is from 6.5 to 8.0; preferably, the pH of coupling is from 6.8 to 7.8; and more preferably, the pH of coupling is from 7.0-7.5, such as 7.1, 7.2, 7.3, and 7.4.

The experimental results show that the antibody is almost not coupled with drug molecule below pH 6. At pH 7.8, a part of the original antibody still remains in which the part with a DAR number of 1 accounts a large portion; while the pH is about 7.0, the main part is that with a DAR number of 2. Therefore, the reaction efficiency is better when the pH is about 7.0.

The C-Lock method: an antibody after reduction by TCEP is directly linked to L-D in a mild solution system. For example, the antibody is reduced with a 5-10 fold excess of TCEP at room temperature and excess TCEP is removed by ultrafiltration. 5-10 times of L-D was added to the reduced antibody solution for reaction, and excess small molecule L-D was removed by ultrafiltration. The antibody-drug conjugate was loaded onto a hydrophobic chromatography column (HIC) and purified to obtain an anti-HER2 antibody-drug conjugate with a coupling number of 4.

The structures of ZV0201, ZV0202, ZV0203, ZV0223 and ZV0230 conjugates prepared in the examples are shown in the following table.

TABLE 1

| | Antibody-drug conjugate structure ||||||
| | Conjugate No. ||||||
| | ZV0201 | ZV0202 | ZV0203 | ZV0204 | ZV0205 | ZV0230 |
|---|---|---|---|---|---|---|
| coupling method | K-Lock | K-Lock | K-Lock | K-Lock | K-Lock | K-Lock |
| L-D | Compound 18 | Compound 33 | Compound 7 | Compound 30 | Compound 37 | Compound 23 |
| n | 1.8-2 | 1.8-2 | 1.8-2 | 1.8-2 | 1.8-2 | 1.8-2 |

One representative K-Lock and one C-Lock antibody-conjugated drug were taken for HIC analysis. The steps are as follows:

TSKgel Butyl-NPR column (4.6 mmID×3.5 cm, 2.5 mm, Tosoh Bioscience, Montgomeryville, PA) was used and mobile phases were 1.5M ammonium sulfate+0.025M sodium phosphate buffer (pH 7) and 75% 0.025M sodium phosphate buffer+25% isopropanol (pH 7.0). Gradient elution: 10% B-70% B, 10 min; 70% B-100% B, 5 min; 100% B-10% B, 2 min.

FIG. 1 shows the results of HIC analysis of the antibody drug conjugates according to the present invention; wherein FIG. 1A shows the results of HIC analysis of unconjugated antibodies; FIG. 1B shows the results of HIC analysis of ZV0201. It can be seen that the purity of conjugates with average coupling number (DAR) of 2 is more than 90%, in which only a small amount of ADC with average coupling number (DAR) of 1 is contained. FIG. 1C shows the results of HIC analysis of C-Lock (ZV0223, preparation method as described above). It can be seen that ADCs with average coupling number of 4 accounts the main part and the purity is greater than 90%.

Peptide mapping analysis of the ADC of the present invention (such as ZV0201) and the analysis parameters are as follows:

samples were digested with trypsin and then subjected to liquid chromatography (column type BEH 300 C18 1.7 um×2.1×150 mm, temperature 40° C., mobile phases 0.1% formic acid/water and 0.1% formic acid/acetonitrile).

Figure 1D:
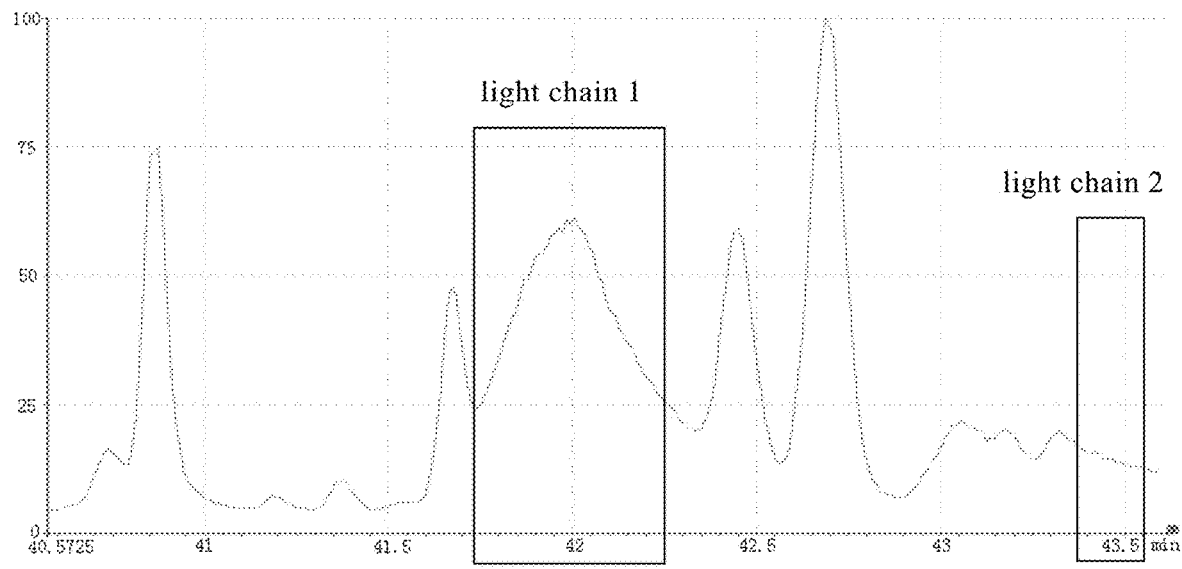
FIG. 1D shows the results of peptide analysis of ZV0201.

The results are shown in FIG. 1D, and in the ADC of the present invention coupled in K-lock mode, drug is mainly coupled to lysine at position 81 of the light chain constant region of the antibody according to the analysis.

Example 11 Affinity Test

Figure 2:
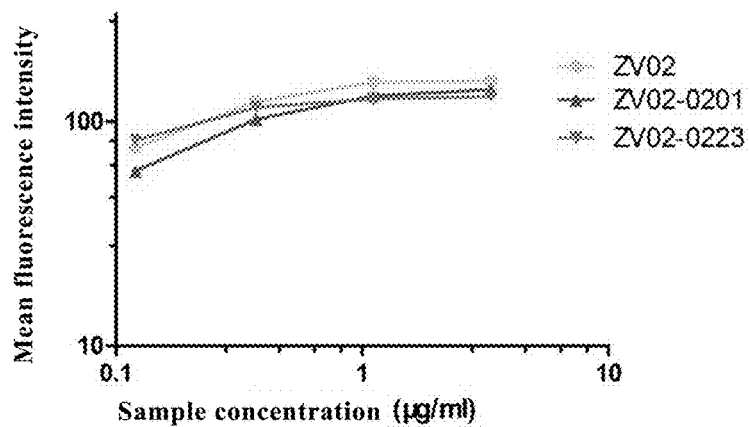
FIG. 2 shows the results of affinity test.

The experimental steps for testing affinity are as follows:
ZV0201 and ZV0223 were diluted to 3.3 µg/ml, and then diluted by a 3-fold gradient at concentrations of 3.3, 1.1, 0.33, and 0.11 µg/ml, respectively, and added to an EP tube containing $3.0 \times 10^5$ BT474 cells, respectively, and incubated at 4° C. for 30 min. The cells were pelleted by centrifugation and washed once with PBS. Then 600 µl of FITC-labeled secondary antibody dilution was added and incubated for 30 min at 4° C. in darkness. The cells were pelleted by centrifugation, washed twice with PBS, and finally, the cells were suspended by adding 500 µl of PBS, and the average fluorescence intensity value was measured by flow cytometry. The test results are as follows:

The affinity of anti-HER2 antibody before and after coupling was compared. K-Lock is represented by ZV0201, C-Lock is represented by ZV0223, and the affinity test results are shown in FIG. 2. It can be seen from the figure that antibody affinity has not changed before and after coupling.

Example 12 Tumor Cell Inhibition Experiment

This example examined the inhibitory activity of the antibody-drug conjugates of the present invention on HER2-positive cells. The tumor cell lines in this example were all purchased from ATCC, USA.

The experimental steps are as follows:
The cells were digested, collected by centrifugation, counted, and the cell liquid was diluted to $0.4$-$2.0 \times 10^5$ cells/ml, and 100 µl of said cell suspension was added to each well of a 96-well plate. The cells were cultured overnight in a 37° C. cell culture incubator, and ADC drugs with corresponding concentration was added the next day. The initial concentration of the drug was 1-15 µg/ml, and was diluted in 3-fold equal-gradient with a total of 9 concentration gradients. Finally, a set of zero-concentration cell were set as controls. After addition of drug, the cells were cultured for 3 days, and the drug-containing medium was sucked. 100 µl of 10% CCK-8 solution was added to each well, and incubated at 37° C. for 1-2 h, and then absorbance intensity of each well was detected at 490 nm with a microplate reader. The data was imported into a mapping software, the curve was fitted, and IC50 values were calculated.

The experimental results are shown in the table below. The cell activity of the ADCs of the present invention is significantly better than that of marketed T-DM1.

TABLE 2

IC50 values (nM) of anti-HER2 antibody-drug conjugates to HER2-expressing tumor cells

| | ZV0201 | ZV0202 | ZV0203 | ZV0230 | T-DM1 |
|---|---|---|---|---|---|
| SKBR-3 HER2 3+ | 0.038 | 0.162 | 0.129 | 0.0844 | 0.114 |
| NCI-N87 HER2 3+ | 0.243 | 1.47 | 0.621 | 3.56 | 0.548 |
| OE-19 HER2 3+ | 0.0586 | 0.196 | 0.296 | 0.196 | 0.099 |
| BT474 HER2 3+ | 0.0731 | / | 0.112 | 0.145 | 0.622 |
| HCC1954 HER2 3+ | 0.033 | 0.070 | 0.214 | 0.232 | 0.159 |
| MDA453 HER2 2+ | 0.0633 | 0.0783 | 0.201 | / | 0.259 |

Cell Cycle Detection Method:
In a 6-well plate, $3.0 \times 10^5$ NCI-N87 cells and a final concentration of 5 µl of ZV0201 were added to each well. After incubation at 37° C. for 60 h, all the cells in a well were collected, and pelleted by centrifugation. 1 mL of 70% ethanol pre-cooled with ice bath was added and fixed overnight at 4° C. After fixation, the cells were washed with PBS once, PI staining solution was added and incubated at 37° C. for 30 min in darkness, and then was detected by flow cytometry.

Figure 3:
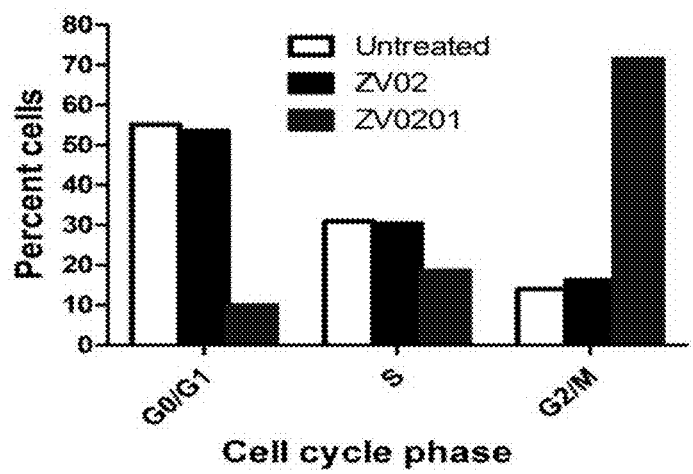
FIG. 3 shows the results of a cell cycle inhibition experiment.

The experimental results showed that under the action of drugs, cell cycles of more than 70% N87 tumor cells stopped in G2/M phase, and the results are shown in FIG. 3. In FIG. 3, ZV02 is an antibody control without conjugating drug.

Example 13 In Vivo Antitumor Activity

Steps for in vivo anti-tumor activity detection of anti-HER2 antibody-drug conjugates are as follows:
Tumor cells were inoculated into the sputum of nude mice or Scid mice. When the tumor volume was 100-300 mm$^3$ in length, drugs were given through tail vein. OE19 was administered in three times, once every three days. Other models were single administration, and tumor sizes were timing-measured after administration. The long diameter (a) and short diameter (b) of a tumor mass were measured, and the tumor volume (TV) was calculated as: TV=1/2×a×b$^2$.

The experimental results show that the anti-HER2 antibody-drug conjugates of the present invention has a significant inhibitory effect on tumors in vivo, and the tumor inhibitory activity in vivo is more than three times higher than that of T-DM1.

Figure 4:
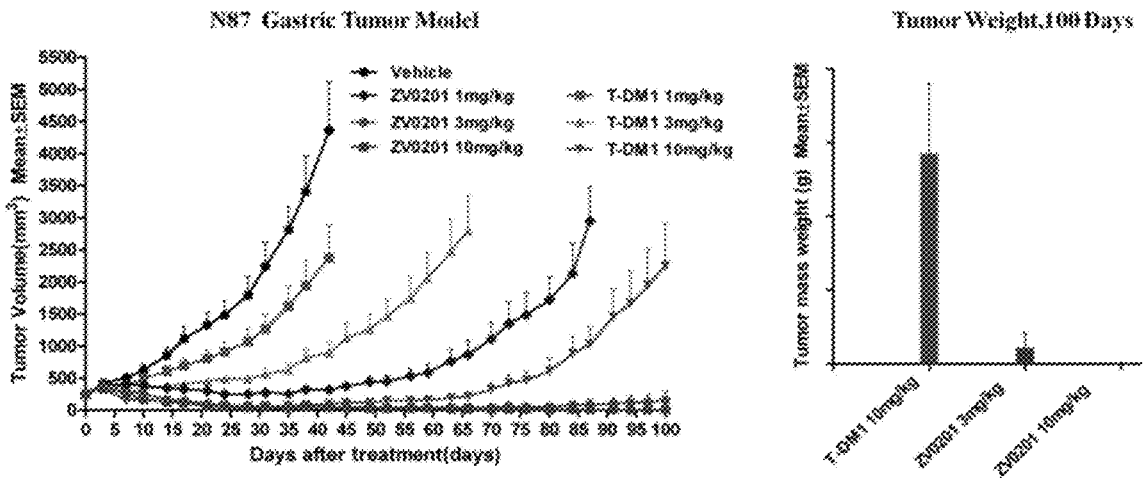
FIG. 4 shows the efficacy of ADC in the treatment of N87 gastric cancer xenograft in mice.

FIG. 4 shows the efficacy of ADC in the treatment of N87 gastric cancer xenograft in mice. All the ADCs of the present invention is effective for inhibiting the growth of N87 tumors, and the K-Lock conjugate of the present invention can completely inhibit the tumor from recurring for dozens of days, and the therapeutic effect is significantly better than that of the marketed T-DM1.

Figure 5:
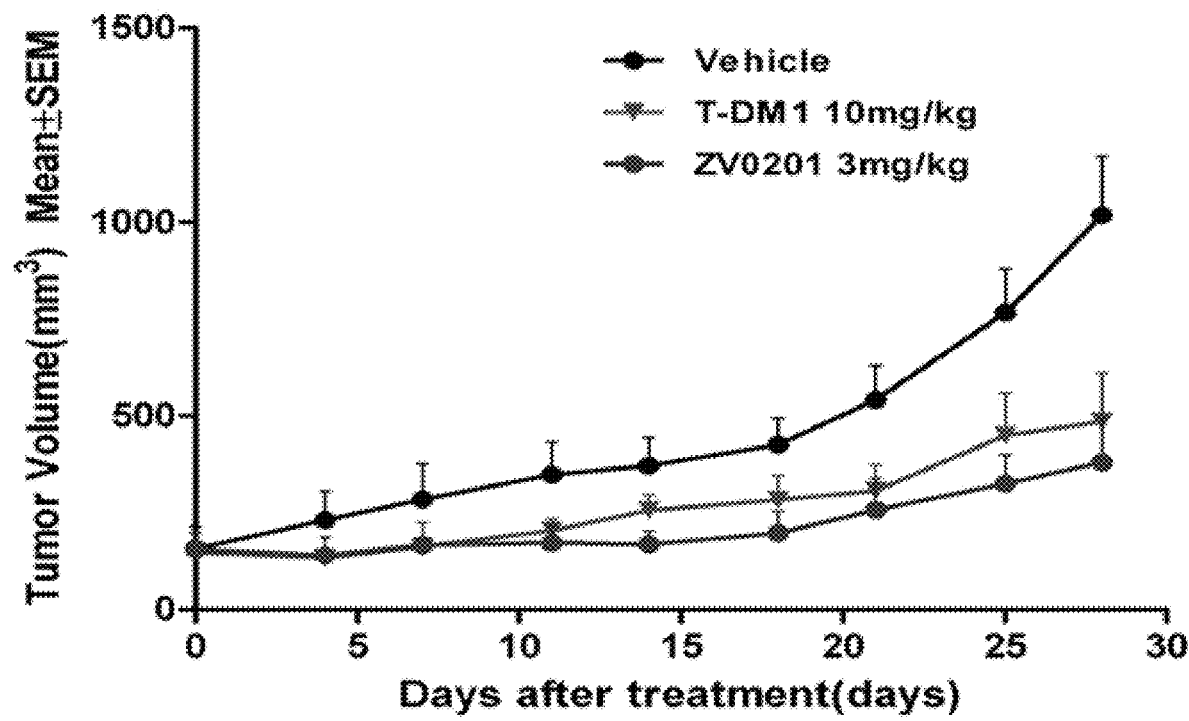
FIG. 5 shows the efficacy of ADC in the treatment of OE19 gastric cancer xenograft in mice.

FIG. 5 shows the efficacy of ADC in the treatment of OE19 gastric cancer xenograft in mice. All the ADCs of the present invention is effective for inhibiting the growth of OE19 tumors, and the ADCs of the present invention can completely inhibit the tumor from recurring for dozens of days, and the therapeutic effect is better than that of the marketed T-DM1.

Figure 6:
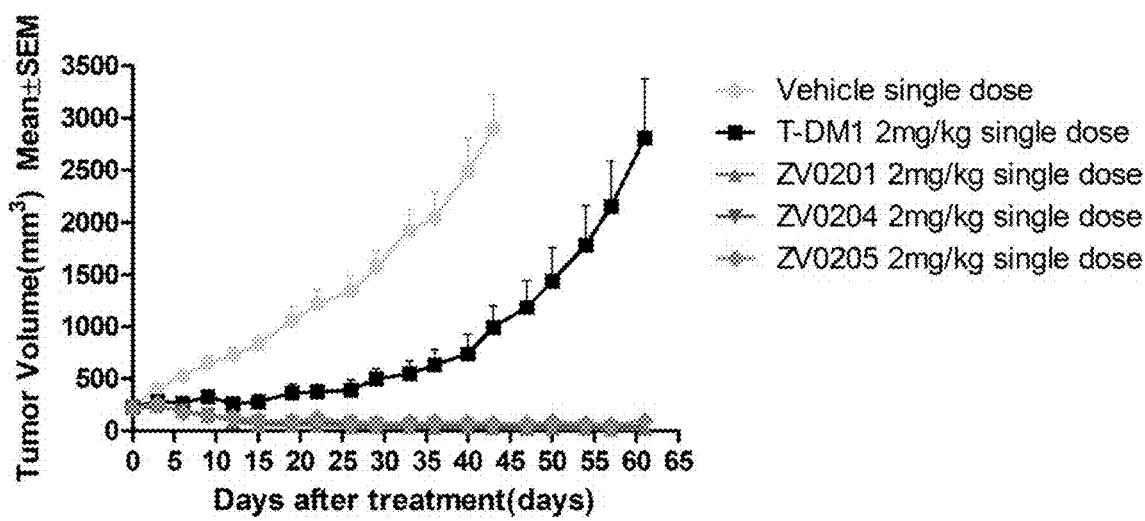
FIG. 6 shows the efficacy of ADC in the treatment of SKOV-3 ovarian cancer xenograft in mice.

FIG. 6 shows the efficacy of ADC in the treatment of SKOV-3 ovarian cancer xenograft in mice. All the ADCs of the present invention is effective for inhibiting the growth of OE19 tumors, and the therapeutic effect of the ADCs of the present invention is better than that of the marketed T-DM1.

Figure 7:
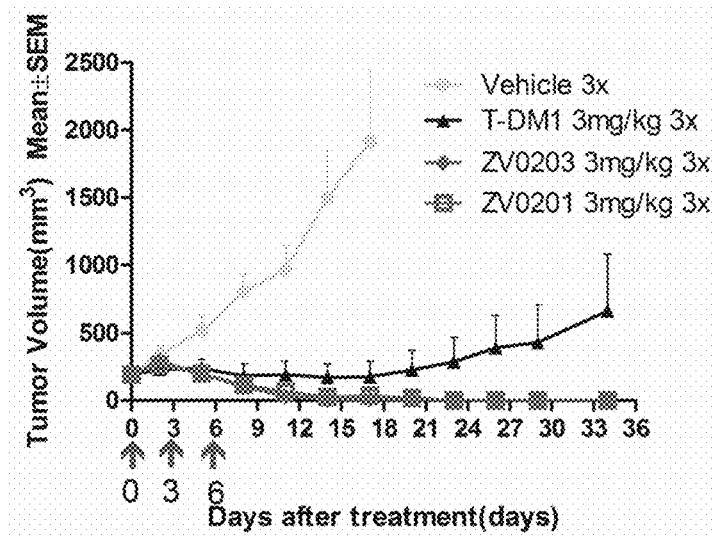
FIG. 7 shows the efficacy of ADC in the treatment of BT474 breast cancer xenograft in mice.

FIG. 7 shows the efficacy of ADC in the treatment of BT474 breast cancer xenograft in mice. All the ADCs of the present invention is effective for inhibiting the growth of BT474 tumors, and the therapeutic effect of Zhaohua ADCs is better than that of the marketed T-DM1.

Figure 8:
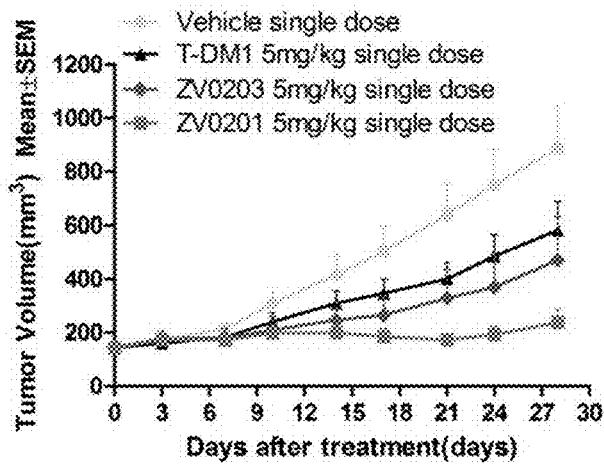
FIG. 8 shows the efficacy of ADC in the treatment of Calu-3 lung cancer xenograft in mice.
Figure 9:
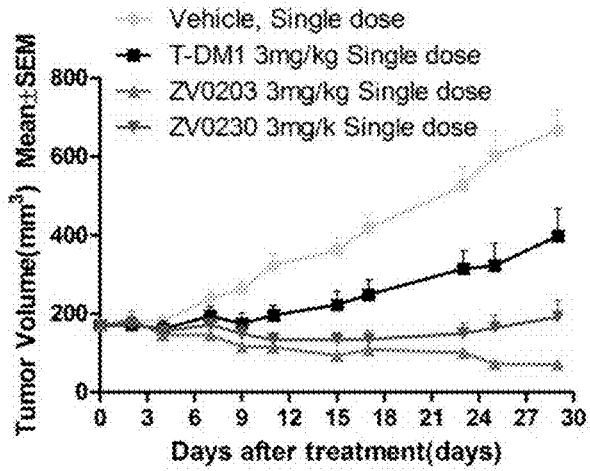
FIG. 9 shows the inhibitory effect of the ADC of the present invention on tumor volume.

FIG. 8 shows the efficacy of ADC in the treatment of Calu-3 lung cancer xenograft in mice. All the ADCs of the present invention is effective for inhibiting the growth of Calu-3 tumors, and the therapeutic effect of the present invention is better than that of the marketed T-DM1.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be in the scope of the invention defined by the appended claims of the application.

The invention claimed is:

1. An antibody-drug conjugate or a pharmaceutically acceptable salt thereof, wherein the structure of the antibody-drug conjugate is as shown in formula I:

Ab-(L-D)n    I wherein:
Ab is an antibody, wherein the antibody is pertuzumab;
L is a linker connecting the antibody and the drug;
  wherein L has a structure of L-1:

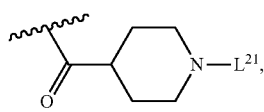
(L-1)

wherein $L^{21}$ is a linker moiety independently selected from the group consisting of Val-Cit, —(CH$_2$)n-, —(CH$_2$CH$_2$O)n-, Ala-Ala-Asn, and a combination thereof, and the wavy line indicates the connection position with antibody
D is a small molecule drug that inhibits tumor cells, and the structure of D is as shown in formula II:

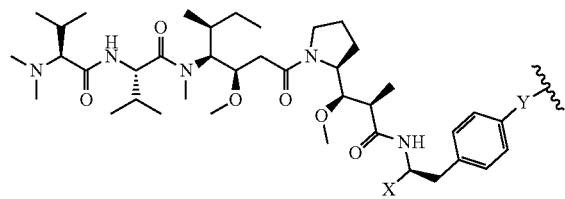
II wherein in formula II, Y is O or NH, and the wavy line indicates the connection position with L, X is CH$_2$N3 or

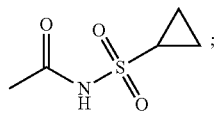

n is an average number of coupled drugs in the antibody-drug, and n is from 1.8 to 2;
the dash marks represent bonds;
wherein the light chain constant region of the antibody comprises a EKH motif and the drug molecule is linked to a lysine (K) residue of the motif.

2. The antibody-drug conjugate of claim 1, wherein the light chain constant region of the antibody comprises YEKHK (SEQ ID NO: 59) motif and the drug molecule is linked to the first lysine (K) site of the motif.

3. The antibody-drug conjugate of claim 1, wherein X is

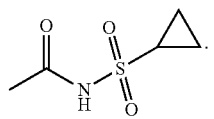

4. The antibody-drug conjugate of claim 1, wherein n is 2.

5. The antibody-drug conjugate of claim 1, wherein X is CH$_2$N$_3$.

6. The antibody-drug conjugate of claim 1, wherein the antibody-drug conjugate is selected from the group consisting of: ZV0201, ZV0202, ZV0203, ZV0204, ZV0205, and ZV0230,
wherein,
the structure of conjugate ZV0203 is shown as follows:

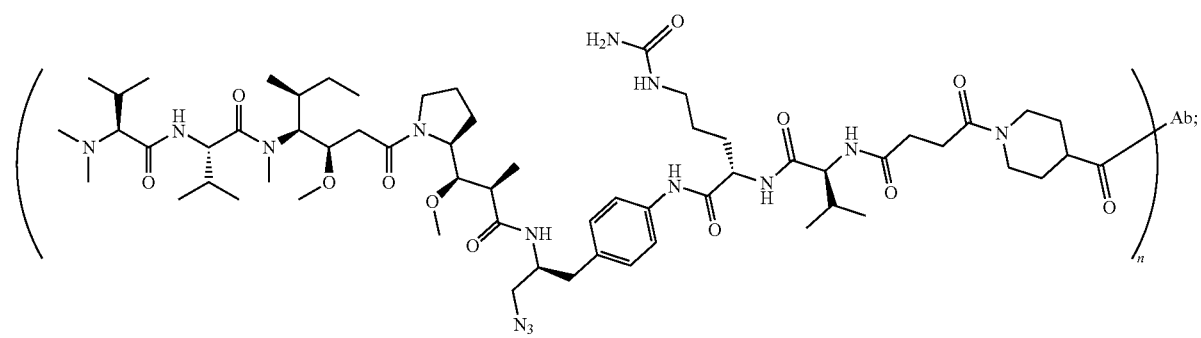

the structure of conjugate ZV0230 is shown as follows:
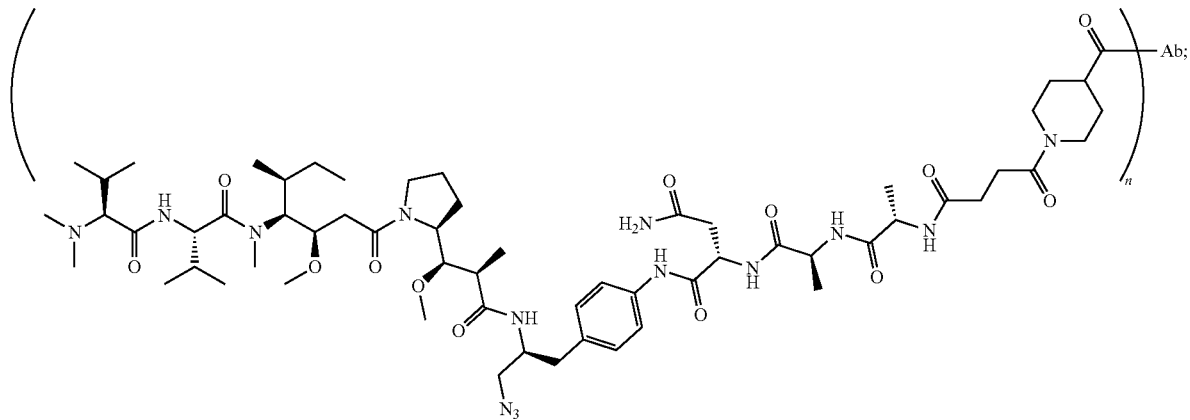
the structure of conjugate ZV0201 is shown as follows:
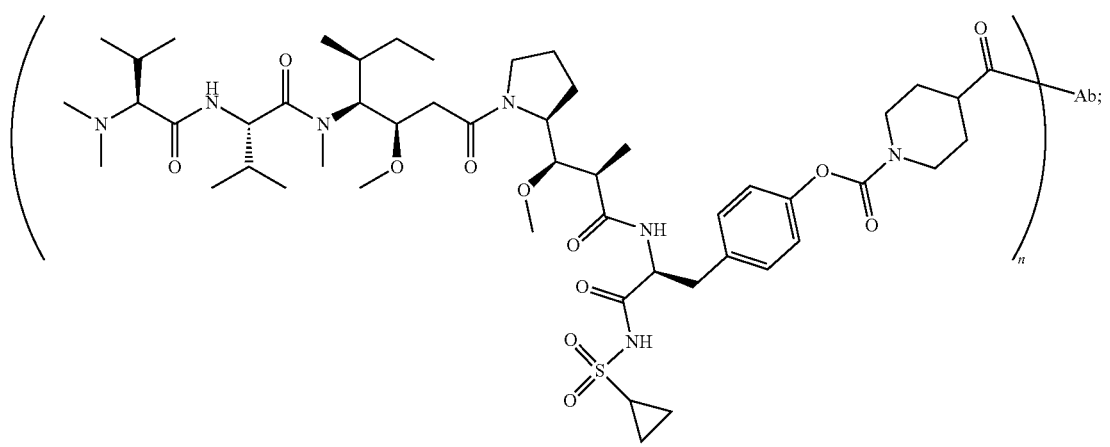
the structure of conjugate ZV0202 is shown as follows:
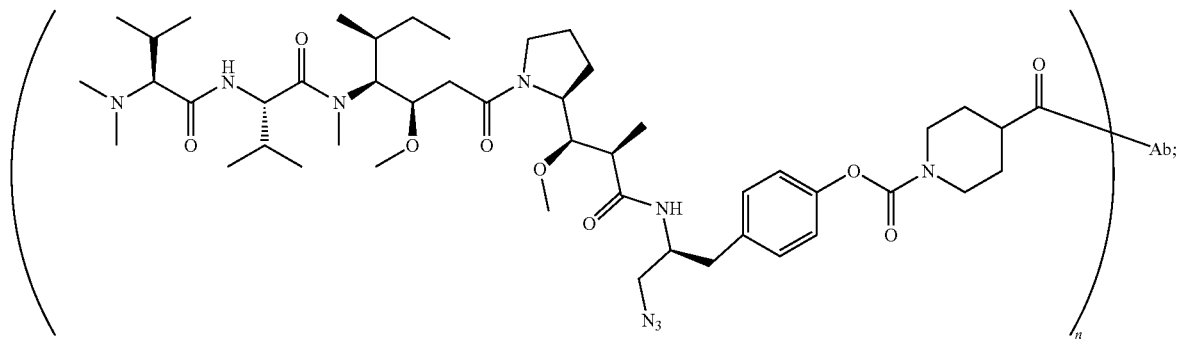

the structure of conjugate ZV0204 is shown as follows:

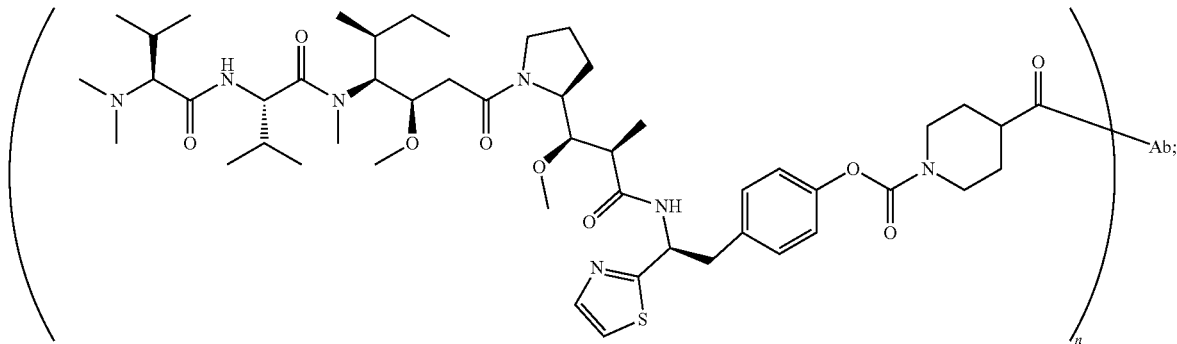

the structure of conjugate ZV0205 is shown as follows:

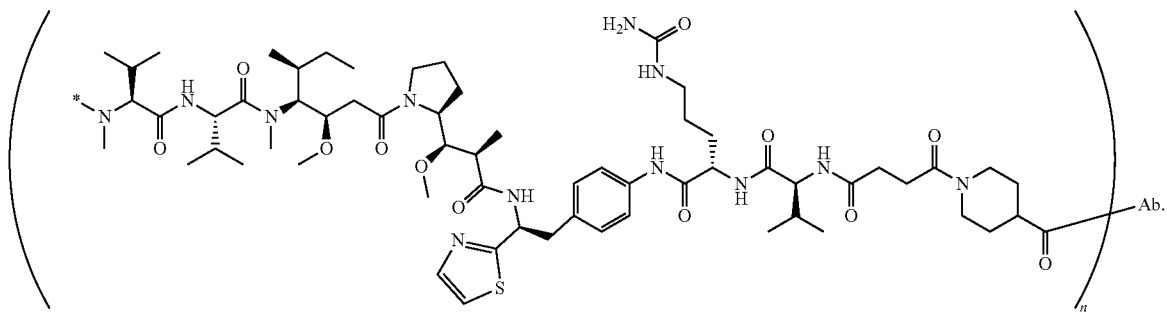

7. The antibody-drug conjugate of claim 6, wherein the antibody-drug conjugate is ZV0203, ZV0204, ZV0205, or ZV0230.

8. The antibody-drug conjugate of claim 6, wherein the antibody-drug conjugate is ZV0201.

9. A pharmaceutical composition which comprises the antibody-drug conjugate of claim 1, and a pharmaceutically acceptable carrier.

10. A preparation method for the antibody-drug conjugate of claim 1, wherein the method comprises the following steps:

configuring a reaction system including an antibody and a free drug molecule, and then performing a coupling reaction to prepare the antibody-drug conjugate, wherein the drug molecule includes a linker.

11. The method of claim 10, wherein the pH of the reaction system is from 6.5 to 8.0.

12. The method of claim 11, wherein the pH is from 6.8 to 7.8.

13. The method of claim 12, wherein the pH is from 6.8 to 7.2.

14. A method of treating a tumor, which comprises a step of administering to a subject in need thereof the antibody-drug conjugate of claim 1, wherein the tumor is breast cancer.

* * * * *

SEQUENCE LISTING

```
<160> NUMBER OF SEQ ID NOS: 60

<210> SEQ ID NO 1
<211> LENGTH: 107
<212> TYPE: PRT
<213> ORGANISM: Artificial sequence
<220> FEATURE:
<223> OTHER INFORMATION: light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 2
<211> LENGTH: 109
<212> TYPE: PRT
<213> ORGANISM: Artificial sequence
<220> FEATURE:
<223> OTHER INFORMATION: light chain variable region

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Leu
            35                  40                  45

Tyr Ser Ala Ser Tyr Arg Tyr Thr Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105

<210> SEQ ID NO 3
```

```
<211> LENGTH: 109
<212> TYPE: PRT
<213> ORGANISM: Artificial sequence
<220> FEATURE:
<223> OTHER INFORMATION: light chain variable region

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Val Ser Ile Gly
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105

<210> SEQ ID NO 4
<211> LENGTH: 109
<212> TYPE: PRT
<213> ORGANISM: Artificial sequence
<220> FEATURE:
<223> OTHER INFORMATION: light chain variable region

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Ser Ile Gly
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105

<210> SEQ ID NO 5
<211> LENGTH: 109
<212> TYPE: PRT
<213> ORGANISM: Artificial sequence
<220> FEATURE:
<223> OTHER INFORMATION: light chain variable region

<400> SEQUENCE: 5

Glu Ile Val Met Thr Gln Ser Pro Pro Thr Leu Ser Leu Ser Pro Gly
1               5                   10                  15

Glu Arg Val Thr Leu Ser Cys Lys Ala Ser Gln Asp Val Ser Ile Gly
            20                  25                  30

Val Ala Trp Tyr Gln Gln Lys Pro Gly Gln Ala Pro Arg Leu Leu Ile
        35                  40                  45
```

```
Tyr Ser Ala Ser Tyr Arg Tyr Thr Ser Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105
```

<210> SEQ ID NO 6
<211> LENGTH: 109
<212> TYPE: PRT
<213> ORGANISM: Artificial sequence
<220> FEATURE:
<223> OTHER INFORMATION: light chain variable region

<400> SEQUENCE: 6

```
Ala Ile Arg Met Thr Gln Ser Pro Ser Ser Phe Ser Ala Ser Thr Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105
```

<210> SEQ ID NO 7
<211> LENGTH: 109
<212> TYPE: PRT
<213> ORGANISM: Artificial sequence
<220> FEATURE:
<223> OTHER INFORMATION: light chain variable region

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105
```

<210> SEQ ID NO 8
<211> LENGTH: 109
<212> TYPE: PRT
<213> ORGANISM: Artificial sequence

```
<220> FEATURE:
<223> OTHER INFORMATION: light chain variable region

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Val Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105
```

```
<210> SEQ ID NO 9
<211> LENGTH: 109
<212> TYPE: PRT
<213> ORGANISM: Artificial sequence
<220> FEATURE:
<223> OTHER INFORMATION: light chain variable region

<400> SEQUENCE: 9

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105
```

```
<210> SEQ ID NO 10
<211> LENGTH: 109
<212> TYPE: PRT
<213> ORGANISM: Artificial sequence
<220> FEATURE:
<223> OTHER INFORMATION: light chain variable region

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60
```

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ile Tyr Pro Tyr
                85                  90                  95

Thr Phe Gly Gly Gly Thr Lys Leu Glu Ile Lys Arg Thr
            100                 105

<210> SEQ ID NO 11
<211> LENGTH: 107
<212> TYPE: PRT
<213> ORGANISM: Artificial sequence
<220> FEATURE:
<223> OTHER INFORMATION: light chain variable region

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 12
<211> LENGTH: 107
<212> TYPE: PRT
<213> ORGANISM: Artificial sequence
<220> FEATURE:
<223> OTHER INFORMATION: light chain variable region

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 13
<211> LENGTH: 107
<212> TYPE: PRT
<213> ORGANISM: Artificial sequence
<220> FEATURE:
<223> OTHER INFORMATION: light chain variable region

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: Artificial sequence
<220> FEATURE:
<223> OTHER INFORMATION: light chain variable region

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 15
<211> LENGTH: 107
<212> TYPE: PRT
<213> ORGANISM: Artificial sequence
<220> FEATURE:
<223> OTHER INFORMATION: light chain variable region

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 16
<211> LENGTH: 107
<212> TYPE: PRT
<213> ORGANISM: Artificial sequence
<220> FEATURE:
<223> OTHER INFORMATION: light chain variable region

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 17
<211> LENGTH: 107
<212> TYPE: PRT
<213> ORGANISM: Artificial sequence
<220> FEATURE:
<223> OTHER INFORMATION: light chain variable region

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 18
<211> LENGTH: 107
<212> TYPE: PRT
<213> ORGANISM: Artificial sequence
<220> FEATURE:
<223> OTHER INFORMATION: light chain variable region

<400> SEQUENCE: 18

Asp Ile Gln Met Thr Gln Ser Pro Ser Ser Leu Ser Ala Ser Val Gly

```
                1               5                  10                 15
            Asp Arg Val Thr Ile Thr Cys Lys Ala Ser Gln Asp Val Ser Ile Gly
                           20                  25                 30

Val Ala Trp Tyr Gln Gln Lys Pro Gly Lys Ala Pro Lys Leu Leu Ile
                           35                  40                 45

Tyr Ser Ala Ser Tyr Arg Tyr Thr Gly Val Pro Ser Arg Phe Ser Gly
                           50                  55                 60

Ser Gly Ser Gly Thr Asp Phe Thr Leu Thr Ile Ser Ser Leu Gln Pro
            65                 70                  75                 80

Glu Asp Phe Ala Thr Tyr Tyr Cys Gln Gln Tyr Tyr Ile Tyr Pro Tyr
                               85                  90                 95

Thr Phe Gly Gln Gly Thr Lys Val Glu Ile Lys
                              100                 105

<210> SEQ ID NO 19
<211> LENGTH: 107
<212> TYPE: PRT
<213> ORGANISM: Artificial sequence
<220> FEATURE:
<223> OTHER INFORMATION: light chain variable region

<400> SEQUENCE: 19

Asp Ile Gln Met Thr Gln Ser Pro Ser Ser Leu Ser Ala Ser Val Gly
            1               5                  10                 15

Asp Arg Val Thr Ile Thr Cys Lys Ala Ser Gln Asp Val Ser Ile Gly
                           20                  25                 30

Val Ala Trp Tyr Gln Gln Lys Pro Gly Lys Ala Pro Lys Leu Leu Ile
                           35                  40                 45

Tyr Ser Ala Ser Tyr Arg Tyr Thr Gly Val Pro Ser Arg Phe Ser Gly
                           50                  55                 60

Ser Gly Ser Gly Thr Asp Phe Thr Leu Thr Ile Ser Ser Leu Gln Pro
            65                 70                  75                 80

Glu Asp Phe Ala Thr Tyr Tyr Cys Gln Gln Tyr Tyr Ile Tyr Pro Tyr
                               85                  90                 95

Thr Phe Gly Gln Gly Thr Lys Val Glu Ile Lys
                              100                 105

<210> SEQ ID NO 20
<211> LENGTH: 107
<212> TYPE: PRT
<213> ORGANISM: Artificial sequence
<220> FEATURE:
<223> OTHER INFORMATION: light chain variable region

<400> SEQUENCE: 20

Asp Ile Gln Met Thr Gln Ser Pro Ser Ser Leu Ser Ala Ser Val Gly
            1               5                  10                 15

Asp Arg Val Thr Ile Thr Cys Lys Ala Ser Gln Asp Val Ser Ile Gly
                           20                  25                 30

Val Ala Trp Tyr Gln Gln Lys Pro Gly Lys Ala Pro Lys Leu Leu Ile
                           35                  40                 45

Tyr Ser Ala Ser Tyr Arg Tyr Thr Gly Val Pro Ser Arg Phe Ser Gly
                           50                  55                 60

Ser Gly Ser Gly Thr Asp Phe Thr Leu Thr Ile Ser Ser Leu Gln Pro
            65                 70                  75                 80

Glu Asp Phe Ala Thr Tyr Tyr Cys Gln Gln Tyr Tyr Ile Tyr Pro Tyr
                               85                  90                 95
```

Thr Phe Gly Gln Gly Thr Lys Val Glu Ile Lys
            100                 105

<210> SEQ ID NO 21
<211> LENGTH: 107
<212> TYPE: PRT
<213> ORGANISM: Artificial sequence
<220> FEATURE:
<223> OTHER INFORMATION: light chain variable region

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 22
<211> LENGTH: 107
<212> TYPE: PRT
<213> ORGANISM: Artificial sequence
<220> FEATURE:
<223> OTHER INFORMATION: light chain variable region

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 23
<211> LENGTH: 107
<212> TYPE: PRT
<213> ORGANISM: Artificial sequence
<220> FEATURE:
<223> OTHER INFORMATION: light chain variable region

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly

```
                    20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 24
<211> LENGTH: 107
<212> TYPE: PRT
<213> ORGANISM: Artificial sequence
<220> FEATURE:
<223> OTHER INFORMATION: light chain variable region

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 25
<211> LENGTH: 107
<212> TYPE: PRT
<213> ORGANISM: Artificial sequence
<220> FEATURE:
<223> OTHER INFORMATION: light chain variable region

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 26
<211> LENGTH: 107
<212> TYPE: PRT
<213> ORGANISM: Artificial sequence
<220> FEATURE:
<223> OTHER INFORMATION: light chain variable region

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 27
<211> LENGTH: 107
<212> TYPE: PRT
<213> ORGANISM: Artificial sequence
<220> FEATURE:
<223> OTHER INFORMATION: light chain variable region

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 28
<211> LENGTH: 107
<212> TYPE: PRT
<213> ORGANISM: Artificial sequence
<220> FEATURE:
<223> OTHER INFORMATION: light chain variable region

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
```

```
                35                  40                  45
Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 29
<211> LENGTH: 107
<212> TYPE: PRT
<213> ORGANISM: Artificial sequence
<220> FEATURE:
<223> OTHER INFORMATION: light chain constant region

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 30
<211> LENGTH: 119
<212> TYPE: PRT
<213> ORGANISM: Artificial sequence
<220> FEATURE:
<223> OTHER INFORMATION: heavy chain variable region

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115
```

<210> SEQ ID NO 31
<211> LENGTH: 119
<212> TYPE: PRT
<213> ORGANISM: Artificial sequence
<220> FEATURE:
<223> OTHER INFORMATION: heavy chain variable region

<400> SEQUENCE: 31

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Thr Met Asp Trp Val Arg Gln Ala Pro Gly Lys Gly Leu Glu Trp Val
        35                  40                  45
Ala Asp Val Asn Pro Asn Ser Gly Gly Ser Ile Tyr Asn Gln Arg Phe
    50                  55                  60
Lys Gly Arg Phe Thr Leu Ser Val Asp Arg Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asn Leu Gly Pro Ser Phe Tyr Phe Asp Tyr Trp Gly Gln Gly
            100                 105                 110
Thr Leu Val Thr Val Ser Ser
        115
```

<210> SEQ ID NO 32
<211> LENGTH: 119
<212> TYPE: PRT
<213> ORGANISM: Artificial sequence
<220> FEATURE:
<223> OTHER INFORMATION: heavy chain variable region

<400> SEQUENCE: 32

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Thr Asp Tyr
            20                  25                  30
Thr Met Asp Trp Val Arg Gln Ala Pro Gly Lys Gly Leu Glu Trp Val
        35                  40                  45
Ala Asp Val Asn Pro Asn Ser Gly Gly Ser Ile Tyr Asn Gln Arg Phe
    50                  55                  60
Lys Gly Arg Phe Thr Leu Ser Val Asp Arg Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asn Leu Gly Pro Ser Phe Tyr Phe Asp Tyr Trp Gly Gln Gly
            100                 105                 110
Thr Leu Val Thr Val Ser Ser
        115
```

<210> SEQ ID NO 33
<211> LENGTH: 119
<212> TYPE: PRT
<213> ORGANISM: Artificial sequence
<220> FEATURE:
<223> OTHER INFORMATION: heavy chain variable region

<400> SEQUENCE: 33

```
Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115

<210> SEQ ID NO 34
<211> LENGTH: 119
<212> TYPE: PRT
<213> ORGANISM: Artificial sequence
<220> FEATURE:
<223> OTHER INFORMATION: heavy chain variable region

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115

<210> SEQ ID NO 35
<211> LENGTH: 119
<212> TYPE: PRT
<213> ORGANISM: Artificial sequence
<220> FEATURE:
<223> OTHER INFORMATION: heavy chain variable region

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60
```

```
Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115

<210> SEQ ID NO 36
<211> LENGTH: 119
<212> TYPE: PRT
<213> ORGANISM: Artificial sequence
<220> FEATURE:
<223> OTHER INFORMATION: heavy chain variable region

<400> SEQUENCE: 36

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Asp Tyr
                 20                  25                  30

Thr Met Asp Trp Val Arg Gln Ala Pro Gly Lys Gly Leu Glu Trp Val
             35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115

<210> SEQ ID NO 37
<211> LENGTH: 119
<212> TYPE: PRT
<213> ORGANISM: Artificial sequence
<220> FEATURE:
<223> OTHER INFORMATION: heavy chain variable region

<400> SEQUENCE: 37

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Thr Asp Tyr
                 20                  25                  30

Thr Met Asp Trp Val Arg Gln Ala Pro Gly Lys Gly Leu Glu Trp Val
             35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115
```

<210> SEQ ID NO 38
<211> LENGTH: 119
<212> TYPE: PRT
<213> ORGANISM: Artificial sequence
<220> FEATURE:
<223> OTHER INFORMATION: heavy chain variable region

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 39
<211> LENGTH: 119
<212> TYPE: PRT
<213> ORGANISM: Artificial sequence
<220> FEATURE:
<223> OTHER INFORMATION: heavy chain variable region

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 40
<211> LENGTH: 119
<212> TYPE: PRT
<213> ORGANISM: Artificial sequence
<220> FEATURE:
<223> OTHER INFORMATION: heavy chain variable region

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ser Asp Val Asn Pro Asn Ser Gly Gly Ser Ile Tyr Asn Gln Arg Phe
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Gly Pro Ser Phe Tyr Phe Asp Tyr Trp Gly Gln Gly
            100                 105                 110

Thr Thr Leu Thr Val Ser Ser
            115
```

<210> SEQ ID NO 41
<211> LENGTH: 119
<212> TYPE: PRT
<213> ORGANISM: Artificial sequence
<220> FEATURE:
<223> OTHER INFORMATION: heavy chain variable region

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Ser Trp Val Arg Gln Ala Pro Gly Lys Gly Leu Glu Trp Val
        35                  40                  45

Ser Asp Val Asn Pro Asn Ser Gly Gly Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Gly Pro Ser Phe Tyr Phe Asp Tyr Trp Gly Gln Gly
            100                 105                 110

Thr Thr Leu Thr Val Ser Ser
            115
```

<210> SEQ ID NO 42
<211> LENGTH: 119
<212> TYPE: PRT
<213> ORGANISM: Artificial sequence
<220> FEATURE:
<223> OTHER INFORMATION: heavy chain variable region

<400> SEQUENCE: 42

```
Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Phe Thr Asp Tyr
            20                  25                  30

Thr Met Asp Trp Val Arg Gln Ala Pro Gly Gln Gly Leu Glu Trp Met
        35                  40                  45

Gly Asp Val Asn Pro Asn Ser Gly Gly Ser Ile Tyr Asn Gln Arg Phe
    50                  55                  60
```

Lys Gly Arg Phe Val Phe Ser Leu Asp Thr Ser Val Ser Met Ala Tyr
 65                  70                  75                  80

Leu Gln Ile Ser Ser Leu Lys Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 43
<211> LENGTH: 119
<212> TYPE: PRT
<213> ORGANISM: Artificial sequence
<220> FEATURE:
<223> OTHER INFORMATION: heavy chain variable region

<400> SEQUENCE: 43

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Phe Thr Asp Tyr
                20                  25                  30

Thr Met Asn Trp Val Arg Gln Ala Pro Gly Gln Gly Leu Glu Trp Met
            35                  40                  45

Gly Asp Val Asn Pro Asn Ser Gly Gly Ser Thr Tyr Ala Gln Gly Phe
        50                  55                  60

Thr Gly Arg Phe Val Phe Ser Leu Asp Thr Ser Val Ser Met Ala Tyr
 65                  70                  75                  80

Leu Gln Ile Ser Ser Leu Lys Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 44
<211> LENGTH: 119
<212> TYPE: PRT
<213> ORGANISM: Artificial sequence
<220> FEATURE:
<223> OTHER INFORMATION: heavy chain variable region

<400> SEQUENCE: 44

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asp Tyr
                20                  25                  30

Thr Met Asp Trp Val Arg Gln Ala Arg Gly Gln Arg Leu Glu Trp Ile
            35                  40                  45

Gly Asp Val Asn Pro Asn Ser Gly Gly Ser Ile Tyr Asn Gln Arg Phe
        50                  55                  60

Lys Gly Arg Val Thr Ile Thr Arg Asp Met Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Asn Leu Gly Pro Ser Phe Tyr Phe Asp Tyr Trp Gly Gln Gly
            100                 105                 110

Thr Thr Leu Thr Val Ser Ser

-continued

```
<210> SEQ ID NO 45
<211> LENGTH: 119
<212> TYPE: PRT
<213> ORGANISM: Artificial sequence
<220> FEATURE:
<223> OTHER INFORMATION: heavy chain variable region

<400> SEQUENCE: 45

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Asp Tyr
            20                  25                  30

Thr Met Gln Trp Val Arg Gln Ala Arg Gly Gln Arg Leu Glu Trp Ile
        35                  40                  45

Gly Asp Val Asn Pro Asn Ser Gly Gly Ser Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 46
<211> LENGTH: 119
<212> TYPE: PRT
<213> ORGANISM: Artificial sequence
<220> FEATURE:
<223> OTHER INFORMATION: heavy chain variable region

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Phe Thr Asp Tyr
            20                  25                  30

Thr Met Asp Trp Val Arg Gln Ala Pro Gly Lys Gly Leu Glu Trp Met
        35                  40                  45

Gly Asp Val Asn Pro Asn Ser Gly Gly Ser Ile Tyr Asn Gln Arg Phe
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 47
<211> LENGTH: 119
<212> TYPE: PRT
<213> ORGANISM: Artificial sequence
<220> FEATURE:
<223> OTHER INFORMATION: heavy chain variable region

<400> SEQUENCE: 47
```

Gln Val Gln Leu Val Gln Ser Gly Ala Glu Val Lys Lys Pro Gly Ala
1               5                   10                  15

Ser Val Lys Val Ser Cys Lys Val Ser Gly Phe Thr Phe Thr Asp Tyr
            20                  25                  30

Thr Met His Trp Val Arg Gln Ala Pro Gly Lys Gly Leu Glu Trp Met
        35                  40                  45

Gly Asp Val Asn Pro Asn Ser Gly Gly Ser Ile Tyr Ala Gln Lys Phe
    50                  55                  60

Gln Gly Arg Val Thr Met Thr Glu Asp Thr Ser Thr Asp Thr Ala Tyr
65              70                  75                  80

Met Glu Leu Ser Ser Leu Arg Ser Glu Asp Thr Ala Val Tyr Tyr Cys
                85                  90                  95

Ala Thr Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 48
<211> LENGTH: 119
<212> TYPE: PRT
<213> ORGANISM: Artificial sequence
<220> FEATURE:
<223> OTHER INFORMATION: heavy chain variable region

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Thr Met Asp Trp Val Arg Gln Ala Pro Gly Gln Gly Leu Glu Trp Met
        35                  40                  45

Gly Asp Val Asn Pro Asn Ser Gly Gly Ser Ile Tyr Asn Gln Arg Phe
    50                  55                  60

Lys Gly Arg Val Thr Ile Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 49
<211> LENGTH: 119
<212> TYPE: PRT
<213> ORGANISM: Artificial sequence
<220> FEATURE:
<223> OTHER INFORMATION: heavy chain variable region

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Thr Ile Ser Trp Val Arg Gln Ala Pro Gly Gln Gly Leu Glu Trp Met
        35                  40                  45

Gly Asp Val Asn Pro Asn Ser Gly Gly Ser Asn Tyr Ala Gln Lys Phe

```
                    50                  55                  60
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Thr Leu Thr Val Ser Ser
            115

<210> SEQ ID NO 50
<211> LENGTH: 119
<212> TYPE: PRT
<213> ORGANISM: Artificial sequence
<220> FEATURE:
<223> OTHER INFORMATION: heavy chain variable region

<400> SEQUENCE: 50

Gln Val Gln Leu Val Gln Ser Gly Ala Glu Val Lys Lys Pro Gly Ala
  1               5                  10                  15

Ser Val Lys Val Ser Cys Lys Ala Ser Gly Phe Thr Phe Thr Asp Tyr
                 20                  25                  30

Thr Met Asp Trp Val Arg Gln Ala Pro Gly Gln Arg Leu Glu Trp Met
             35                  40                  45

Gly Asp Val Asn Pro Asn Ser Gly Gly Ser Ile Tyr Asn Gln Arg Phe
         50                  55                  60
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Thr Leu Thr Val Ser Ser
            115

<210> SEQ ID NO 51
<211> LENGTH: 119
<212> TYPE: PRT
<213> ORGANISM: Artificial sequence
<220> FEATURE:
<223> OTHER INFORMATION: heavy chain variable region

<400> SEQUENCE: 51

Gln Val Gln Leu Val Gln Ser Gly Ala Glu Val Lys Lys Pro Gly Ala
  1               5                  10                  15

Ser Val Lys Val Ser Cys Lys Ala Ser Gly Phe Thr Phe Thr Asp Tyr
                 20                  25                  30

Thr Met His Trp Val Arg Gln Ala Pro Gly Gln Arg Leu Glu Trp Met
             35                  40                  45

Gly Asp Val Asn Pro Asn Ser Gly Gly Ser Lys Tyr Ser Gln Lys Phe
         50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110
```

```
Thr Thr Leu Thr Val Ser Ser
        115

<210> SEQ ID NO 52
<211> LENGTH: 119
<212> TYPE: PRT
<213> ORGANISM: Artificial sequence
<220> FEATURE:
<223> OTHER INFORMATION: heavy chain variable region

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Thr Met Asp Trp Val Arg Gln Ala Pro Gly Gln Gly Leu Glu Trp Met
        35                  40                  45

Gly Asp Val Asn Pro Asn Ser Gly Gly Ser Ile Tyr Asn Gln Arg Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 53
<211> LENGTH: 119
<212> TYPE: PRT
<213> ORGANISM: Artificial sequence
<220> FEATURE:
<223> OTHER INFORMATION: heavy chain variable region

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Thr Met His Trp Val Arg Gln Ala Pro Gly Gln Gly Leu Glu Trp Met
        35                  40                  45

Gly Asp Val Asn Pro Asn Ser Gly Gly Ser Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 54
<211> LENGTH: 119
<212> TYPE: PRT
<213> ORGANISM: Artificial sequence
<220> FEATURE:
<223> OTHER INFORMATION: heavy chain variable region
```

-continued

```
<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Thr Met Asp Trp Val Arg Gln Ala Thr Gly Gln Gly Leu Glu Trp Met
        35                  40                  45

Gly Asp Val Asn Pro Asn Ser Gly Gly Ser Ile Tyr Asn Gln Arg Phe
    50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 55
<211> LENGTH: 119
<212> TYPE: PRT
<213> ORGANISM: Artificial sequence
<220> FEATURE:
<223> OTHER INFORMATION: heavy chain variable region

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Thr Ile Asn Trp Val Arg Gln Ala Thr Gly Gln Gly Leu Glu Trp Met
        35                  40                  45

Gly Asp Val Asn Pro Asn Ser Gly Gly Ser Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 56
<211> LENGTH: 119
<212> TYPE: PRT
<213> ORGANISM: Artificial sequence
<220> FEATURE:
<223> OTHER INFORMATION: heavy chain variable region

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Tyr
            20                  25                  30

Thr Met Asp Trp Val Arg Gln Ala Pro Gly Gln Gly Leu Glu Trp Met
        35                  40                  45
```

Gly Asp Val Asn Pro Asn Ser Gly Gly Ser Ile Tyr Asn Gln Arg Phe
        50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Thr Leu Thr Val Ser Ser
        115

<210> SEQ ID NO 57
<211> LENGTH: 119
<212> TYPE: PRT
<213> ORGANISM: Artificial sequence
<220> FEATURE:
<223> OTHER INFORMATION: heavy chain variable region

<400> SEQUENCE: 57

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Thr Asp Tyr
                 20                  25                  30

Thr Met His Trp Val Arg Gln Ala Pro Gly Gln Gly Leu Glu Trp Met
             35                  40                  45

Gly Asp Val Asn Pro Asn Ser Gly Gly Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Thr Leu Thr Val Ser Ser
        115

<210> SEQ ID NO 58
<211> LENGTH: 329
<212> TYPE: PRT
<213> ORGANISM: Artificial sequence
<220> FEATURE:
<223> OTHER INFORMATION: heavy chain constant region

<400> SEQUENCE: 58

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

```
            Pro Ala Pro Glu Leu Leu Gly Gly Pro Ser Val Phe Leu Phe Pro Pro
                        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
            145                 150                 155                 160

Tyr Val Asp Gly Val Glu Val His Asn Ala Lys Thr Lys Pro Arg Glu
                            165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
            225                 230                 235                 240

Met Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
            305                 310                 315                 320

Gln Lys Ser Leu Ser Leu Ser Pro Gly
                            325

<210> SEQ ID NO 59
<211> LENGTH: 5
<212> TYPE: PRT
<213> ORGANISM: Artificial sequence
<220> FEATURE:
<223> OTHER INFORMATION: motif in light chain constant region

<400> SEQUENCE: 59

Tyr Glu Lys His Lys
1               5

<210> SEQ ID NO 60
<211> LENGTH: 7
<212> TYPE: PRT
<213> ORGANISM: Artificial sequence
<220> FEATURE:
<223> OTHER INFORMATION: motif in light chain constant region

<400> SEQUENCE: 60

Ala Asp Tyr Glu Lys His Lys
1               5
```